(12) United States Patent
Gut et al.

(10) Patent No.: US 6,268,129 B1
(45) Date of Patent: *Jul. 31, 2001

(54) METHOD OF NUCLEIC ACID ANALYSIS

(75) Inventors: Ivo G. Gut, Berlin (DE); Stephan A. Beck, Cambridge (GB)

(73) Assignee: Imperial Cancer Research Technology Limited, London (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/894,836

(22) PCT Filed: Mar. 4, 1996

(86) PCT No.: PCT/GB96/00476

§ 371 Date: Nov. 24, 1997

§ 102(e) Date: Nov. 24, 1997

(87) PCT Pub. No.: WO96/27681

PCT Pub. Date: Sep. 12, 1996

(30) Foreign Application Priority Data

Mar. 3, 1995 (GB) .................................................. 9504598

(51) Int. Cl.$^7$ ..................................................... C12Q 1/68

(52) U.S. Cl. ........................... 435/6; 435/91.2; 536/24.3; 536/25.3; 536/26.6

(58) Field of Search .................... 435/6, 91.2; 536/24.3, 536/26.6, 25.3

(56) References Cited

U.S. PATENT DOCUMENTS 5,849,542  12/1998  Reeve et al. .

FOREIGN PATENT DOCUMENTS

| | | |
|---|---|---|
| 360 676 | 3/1990 | (EP) . |
| 89/12694 | 12/1989 | (WO) . |
| 92/20348 | 11/1992 | (WO) . |
| 93/23415 | 11/1993 | (WO) . |
| 94/16101 | 7/1994 | (WO) . |
| 94/19363 | 9/1994 | (WO) . |
| 95/04160 | 2/1995 | (WO) . |
| 94/14108 | 5/1995 | (WO) . |

OTHER PUBLICATIONS

Goodchild, Bioconjugate Chemistry, 1(3):165–187 May 1990.*

Hodges et al., "'Post–assay' covalent labeling of phosphorothioate–containing nucleic acids with multiple fluorescent markers," Biochemistry, vol. 28, pp. 261–267 (1989).

Cosstick et al., "Fluorescent labeling of tRNA and oligodeoxynucleotides using T4 RNA ligase," Nucl. Ac. Res., vol. 12, No. 4, pp. 1791–1810 (1984).

Keough et al., "Antisense DNA oligonucleotides II: the use of matrix–assisted laser . . . ," Rapid Comm. Mass Spectrum, vol. 7, pp. 195–200 (1993).

Fidanza & McLaughlin, "Introduction of reporter groups at specific sites in DNA containing phosphorothioate diesters," J. Am. Chem. Soc., vol. 111, pp. 9117–9119 (1989).

Nakayame et al., "Direct sequencing of polymerase chain reaction amplified DNA fragments . . . ," Nucl. Ac. Res., vol. 16, pp. 9947–9959 (1988).

(List continued on next page.)

*Primary Examiner*—Scott W. Houtteman
(74) *Attorney, Agent, or Firm*—Nixon & Vanderhye P.C.

(57) ABSTRACT

A method of analysing a nucleic acid by mass spectrometry comprising the steps of: (1) preparing a nucleic acid molecule comprising a negatively charged non-phosphate sugar-sugar linkage; (2) eliminating the charge from all, or up to all but ten, of the sugar-sugar linkages of the said nucleic acid molecule; (3) introducing the said nucleic acid molecule in which the charge has been wholly or partly eliminated as said into a mass spectrometer; and (4) determining the mass of the said nucleic acid molecule. Preferably, the nucleic acid has no or one charge. A method of preparing a nucleic acid molecule containing no or up to ten negative charges and no or up to ten positive charges comprising the steps of (1) synthesizing a nucleic acid with a phosphorothioate linkage or a phosphoroselenoate linkage between sugar residues, and (2) reacting the said nucleic acid with an alkylating agent so as to eliminate the charge on the said phosphorothioate linkage or said phosphoroselenoate linkage. The methods are useful for DNA sequencing and mutation analysis, and the nucleic acids are useful to suppress gene expression.

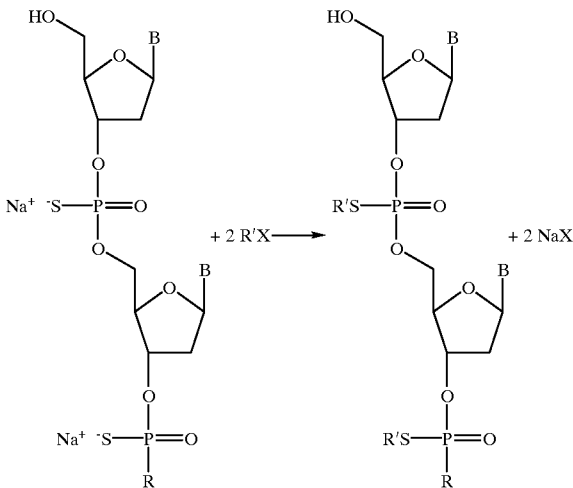

44 Claims, 31 Drawing Sheets

OTHER PUBLICATIONS

Gish & Eckstein, "DNA and RNA sequence determination based on phosphorothioate chemistry," Science, vol. 240, pp. 1520–1522 (1988).

Currie & Yates, "Analysis of oligonucleotides by negative–ion matrix–assisted laser desorption mass spectrometry," J. Am. Soc. Spectrom, vol. 4, pp. 955–963 (1993).

Hathaway, G., "Characterization of modified and normal deoxyoligonucleotides by MALDI, time of flight mass spectrometry," Biotechniques, vol. 17, No. 1, pp. 150–155 (1994).

Eckstein & Gish, "Phosphorothioates in molecular biology," TIBS, vol. 14, pp. 97–100 (1989).

Gut & Beck, "A procedure for selective DNA alkylation and detection by mass spectrometry," Nucl. Ac. Res., vol. 23, pp. 1367–1373 (1995).

Weltman & Karim, "New method for ligand–targeted delivery of phosphorothioate nucleosides," Genet. Eng. News, 14 (1995).

English & Gauss, "Chemically modified oligonucleotides as probes and inhibitors (part only)," vol. 30, No. 6, pp. 613–722 (1991).

Gut & Beck in Griffin & Griffin, "Molecular biology: current innovations and future trends," Horizon Scientific Press, Wymondham, UK, Part I, pp. 147–157 (1995).

Baker et al., "Antisense DNA Oligonucleotides I: the Use of Ionspray . . . ," Rapid Comm. Mass Spectrum., vol. 7, pp. 190–194 (1993).

Labeit et al., "Laboratory Methods: A New Method of DNA . . . ," DNA, vol. 5, No. 2, pp. 173–177 (1986).

Karas & Hillenkamp, "Laser desorption ionization of proteins . . . ," Anal. Comm., vol. 60, pp. 2299–2301 (1988).

Beavis & Chait, "Rapid, sensitive analysis of . . . ," Proc. Natl. Acad. Sci. USA, vol. 87, pp. 6873–6877 (1990).

Karas & Bahr, "Laser desorption ionization mass spectrometry of large biomolecules," Trends in Anal. Chem., vol. 9, pp. 321–325 (1990).

Nelson et al., "Time–of–flight mass spectrometry of nucleic acids by laser . . . ," Rapid Commun. Mass Spectrom., vol. 4, pp. 348–351 (1990).

Splenger et al., "Molecular weight determination of underivatized oligodeoxyribonucleotides by positive . . . ," Commun. Mass Spectrom., vol. 4, pp. 99–102 (1990).

Schieltz et al., "Mass spectrometry of DNA mixtures by laser ablation from frozen aqueous solution," Rapid Commun. Mass Spectrom., vol. 6, pp. 631–636 (1992).

Parr et al., "Matrix–assisted laser desorption/ionization mass spectrometry of synthetic oligodeoxyribonucleotides," Rapid Commun. Mass Spectrom., vol. 6, pp. 369–372 (1992).

Nordhoff et al., "Matrix–assisted laser desoprtion/ionization mass spectrometry of nucleic acids . . . ," Rapid Commun. Mass Spectrom., vol. 6, pp. 771–776 (1992).

Huth–Fehre et al., "Matrix–assisted laser desorption mass spectrometry of oligodeoxythymidylic acids," Rapid Commun. Mass Spectrom., vol. 6, pp. 209–213 (1992).

Fitzgerald et al., "The analysis of mock DNA sequencing reactions using matrix–assisted laser . . . ," Rapid Commun. Mass Spectrom., vol. 7, pp. 895–897 (1993).

Tang et al., "Laser mass spectrometry of polydeoxyribothymidylic acid mixtures," Rapid Commun. Mass Spectrom., vol. 7, pp. 63–66 (1993).

Tang et al., "Matrix–assisted laser desorption ionization of oligonucleotides with various matrices," Rapid Commun. Mass Spectrom., vol. 7, pp. 943–948 (1993).

Stemmler et al., "Matrix–assisted laser desorption/ionization fourier–transform mass . . . ," Rapid Commun. Mass Spectrom., vol. 7, pp. 828–836 (1993).

Smith, L.M., "The future of DNA sequencing," Science, vol. 262, pp. 530–532 (1993).

Fidanza & McLaughlin, "Use of a thiol tether for the site–specific attachment of reporter groups to DNA," J. Org. Chem., vol. 57, pp. 2340–2346 (1992).

* cited by examiner

Masses of Alkylated Phosphorothioate Oligonucleotides

| | Free acid | | | CH$_3$I alkylation products | | | | C$_2$H$_5$I alkylation products | | | | C$_3$H$_7$I alkylation products | | | |
|---|---|---|---|---|---|---|---|---|---|---|---|---|---|---|---|
| | calculated | | measured | calculated | | measured | | calculated | | measured | | calculated | | measured | |
| | NIM | PIM | NIM | NIM | PIM | NIM | PIM | NIM | PIM | NIM | PIM | NIM | PIM | NIM | PIM |
| HO-dT$_3$ | 883 | 885 | 885 | 897 | 913 | 891 | 943 (4x) | 911 | 941 | 913 | 971,995 (3x,4x) | 925 | 969 | 925 | 1008 (3x) |
| HO-dC$_3$ | 836 | 838 | 838 | 850 | 866 | - | 896 (4x) | 864 | 894 | 865 | 928 (3x) | 878 | 922 | - | 964 (3x) |
| HO-dG$_3$ | 956 | 958 | 957 | 970 | 986 | - | 1030 (5x) | 984 | 1014 | - | 1048,1071 (3x,4x) | 998 | 1042 | 1001 | 1076 (3x) |
| HO-dA$_3$ | 908 | 910 | 906 | 922 | 938 | - | 994 (6x) | 936 | 966 | 932 | 998 (3x) | 950 | 994 | - | 1026 (3x) |
| HO-dAGCT | 1220 | 1222 | 1218 | 1248 | 1264 | | | 1276 | 1306 | 1277 | 1332 (4x) | 1304 | 1348 | | |
| Hexyl-dAGCT | 1400 | 1402 | 1398 | 1442 | 1458 | | | 1484 | 1514 | 1485 | 1518,1542 (4x,5x) | 1526 | 1570 | | |
| HO-dT$_{10}$ | 3121 | 3123 | 3118 | 3233 | 3249 | | | 3345 | 3375 | 3349 | 3436 (11x) | 3499 | 3543 | | |
| HO-dCTCGA$_{13}$ | 3818 | 3820 | 3816 | 3958 | 3974 | | | 4098 | 4128 | 4101 | 4129,4161 (11x,12x) | 4280 | 4324 | | |

Fig. 7

DNA sequencing by MALDI MS

Enzymatic Generation of a Sequence Ladder

Termination with ddTTP (or modified ddTTP)

| Primer | bold/italic |
|---|---|
| Terminator | bold |
| TEM = | template | a) + b) annealing of primer + enzymatic extention

TEM TCAGTGACAGTAGCACTAGTCATCTGACTTAGCCAGTCATGGACCAGT
 1 *AGTCACTGTCATCGTGATCAGT*
 2 *AGTCACTGTCATCGTGATCAGTAGACT*
 3 *AGTCACTGTCATCGTGATCAGTAGACTGAAT*
 4 *AGTCACTGTCATCGTGATCAGTAGACTGAATCGGT*
 5 *AGTCACTGTCATCGTGATCAGTAGACTGAATCGGTCAGT*
 6 *AGTCACTGTCATCGTGATCAGTAGACTGAATCGGTCAGTACCT*
 7 *AGTCACTGTCATCGTGATCAGTAGACTGAATCGGTCAGTACCTGGT* c) purification and isolation of extended DNA

1 CAGT
 2 CAGTAGACT
 3 CAGTAGACTGAAT
 4 CAGTAGACTGAATCGGT
 5 CAGTAGACTGAATCGGTCAGT
 6 CAGTAGACTGAATCGGTCAGTACCT
 7 CAGTAGACTGAATCGGTCAGTACCTGGT d) alkylation/modification e) preparation of matrix

Fig. 10A f) mass analysis

Mass differences calculated for ethylated phosphorothioate DNA

| | | |
|---|---|---|
| 2 – 1 | 1768 Da |
| 3 – 2 | 1435 Da |
| 4 – 3 | 1427 Da |
| 5 – 4 | 1411 Da |
| 6 – 5 | 1371 Da |
| 7 – 6 | 1094 Da |

Mass differences  1768  1435  1427  1411  1371  1094

Termination with ddGTP (or modified ddGTP)

a) + b) annealing of primer + enzymatic extention

```
TEM  TCAGTGACAGTAGCACTAGTCATCTGACTTAGCCCAGTCATGGACCAGT
  1  AGTCACTGTCATCGTGATCAG
  2  AGTCACTGTCATCGTGATCAGTAG
  3  AGTCACTGTCATCGTGATCAGTAGACTG
  4  AGTCACTGTCATCGTGATCAGTAGACTGAATCG
  5  AGTCACTGTCATCGTGATCAGTAGACTGAATCGTCAG
  6  AGTCACTGTCATCGTGATCAGTAGACTGAATCGTCAGTACCTG
  7  AGTCACTGTCATCGTGATCAGTAGACTGAATCGTCAGTACCTGG
``` c) purification and isolation of extended DNA

```
1  CAG
2  CAGTAG
3  CAGTAGACTG
4  CAGTAGACTGAATCG
5  CAGTAGACTGAATCGG
6  CAGTAGACTGAATCGGTCAG
7  CAGTAGACTGAATCGGTCAGTACCTG
8  CAGTAGACTGAATCGGTCAGTACCTGG
``` d) alkylation/modification

Fig. 10C

Termination with ddCTP (or modified ddCTP)

a) + b) annealing of primer + enzymatic extention

TEM TCAGTGACAGTAGCACTAGTCATCTGACTTAGCCAGTCATGGACCAGT
1 AGTCACTGTCATCGTGATC
2 AGTCACTGTCATCGTGATCAGTAGAC
3 AGTCACTGTCATCGTGATCAGTAGACTGAATC
4 AGTCACTGTCATCGTGATCAGTAGACTGAATCGGTC
5 AGTCACTGTCATCGTGATCAGTAGACTGAATCGGTCAGTAC
6 AGTCACTGTCATCGTGATCAGTAGACTGAATCGGTCAGTACC
7 AGTCACTGTCATCGTGATCAGTAGACTGAATCGGTCAGTACCTGGTC c) purification and isolation of extended DNA

1 C
2 CAGTAGAC
3 CAGTAGACTGAATC
4 CAGTAGACTGAATCGGTC
5 CAGTAGACTGAATCGGTCAGTAC
6 CAGTAGACTGAATCGGTCAGTACC
7 CAGTAGACTGAATCGGTCAGTACCTGGC d) alkylation/modification e) preparation of matrix

Fig. 10E f) mass analysis

Mass differences calculated for ethylated phosphorothioate DNA

2 – 1   2498 Da
3 – 2   2116 Da
4 – 3   1427 Da
5 – 4   1768 Da
6 – 5    333 Da
7 – 6   1427 Da

Termination with ddATP (or modified ddATP)

a) + b) annealing of primer + enzymatic extention

TEM TCAGTGACAGTAGCACTAGTCATCTGACTTAGCCAGTCATGGACCAGT
1  AGTCACTGTCATCGTGATCA
2  AGTCACTGTCATCGTGATCAGTA
3  AGTCACTGTCATCGTGATCAGTAGA
4  AGTCACTGTCATCGTGATCAGTAGACTGA
5  AGTCACTGTCATCGTGATCAGTAGACTGAA
6  AGTCACTGTCATCGTGATCAGTAGACTGAATCGGTCA
7  AGTCACTGTCATCGTGATCAGTAGACTGAATCGGTCAGTA
8  AGTCACTGTCATCGTGATCAGTAGACTGAATCGGTCAGTACCTGGTCA c) purification and isolation of extended DNA

1  CA
2  CAGTA
3  CAGTAGA
4  CAGTAGACTGA
5  CAGTAGACTGAA
6  CAGTAGACTGAATCGGTCA
7  CAGTAGACTGAATCGGTCAGTA
8  CAGTAGACTGAATCGGTCAGTACCTGGTCA d) alkylation/modification e) preparation of matrix

Fig. 10G

Polymerase Chain Reaction (PCR) analysis by MALDI MS a) - e) annealing of primer 1 to template strand, extention, melting of double strand, annealing of primer 1 to template and primer 2 to extention product, extention - multiple cycles

```
TEM   TCGAGGTTACCTGATGACTGATCGGTGAAGCCTGAATTGTGCA
PRIM1 AGCTCCAATGGACTACTGACTAGCCACTTCGGACTTAACACGT
PRIM2 TCGAGGTTACCTGATGACTGATCGGTGAAGCCTGAATTGTGCA
``` f) removal of primers

```
PRIM1           ACTAGCCACTTCGGACTTAACACGT
PRIM2 TCGAGGTTACCTGATGACTGATCGG
``` g) alkylation/modification h) mix with matrix material

Fig. 11A i) mass analysis

Mass caculation for ethylated phosphorothioate DNA  PRIM1 product 8635 Da
                                                    PRIM2 product 8762 Da finger print 8635  8662 mass difference 127 Da Mass differences
point mutations (absolute mass differences in Da):

|   | T   | C   | G   | A   |
|---|-----|-----|-----|-----|
| T | 0   | -15 | +25 | +9  |
| C | +15 | 0   | +40 | +24 |
| G | -25 | -40 | 0   | -16 |
| A | -9  | -24 | +16 | 0   | fingerprint mass differences on point mutations in Da (example):

|   | T | C | G | A |
|---|---|---|---|---|
| T | 0 | 96 | 176 | 145 |
| C | 159 | 0 | 207 | 176 |
| G | 78 | 47 | 0 | 96 |
| A | 109 | 78 | 158 | 0 | deletions (absolute mass differences):

| T | −303 Da |
|---|---|
| C | −288 Da |
| G | −328 Da |
| A | −312 Da | fingerprint mass differences on deletions (example):

| T | 136 Da |
|---|---|
| C | 167 Da |
| G | 87 Da |
| A | 118 Da |

Fig. 11C

Nucleotides
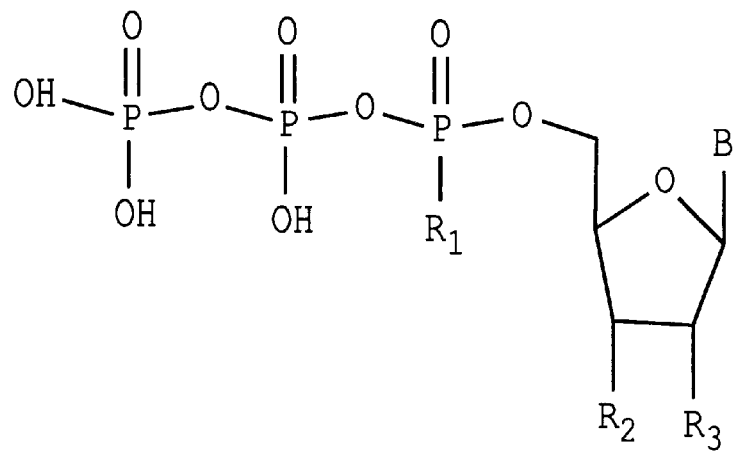
$R_1$ = OH, SH, SeH, BH$_2$, NH$_2$, PH$_3$, F, CI, CH$_3$, OCH$_3$, CN, H
$R_2$ = H, OH, NH$_2$
$R_3$ = H, OH, NH$_2$
B =
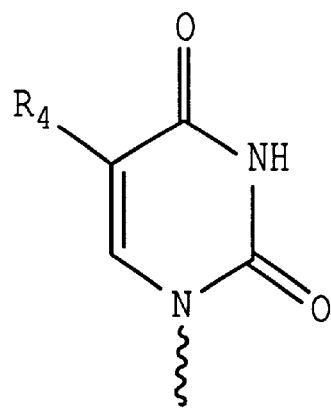 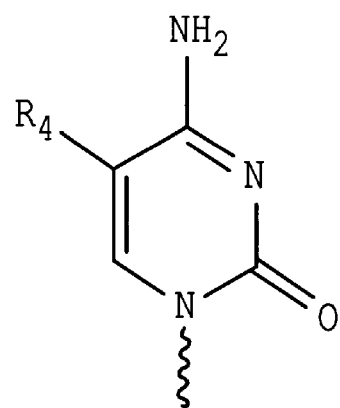
$R_4$ = H, OH$_3$, charged tag
Fig. 12A $R_5$= N,CH$_2$,charged tag $R_6$= H,NH$_2$ substituted i.e.halogenated versions of the nucleotides Alkylating agents $$R_7—Hal$$

$R_7$=alkyl ($CH_3$, $C_2H_5$, secondary, tertiary, substituted...),

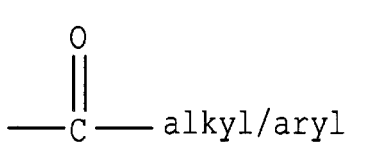

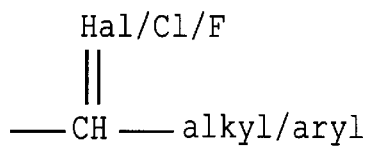

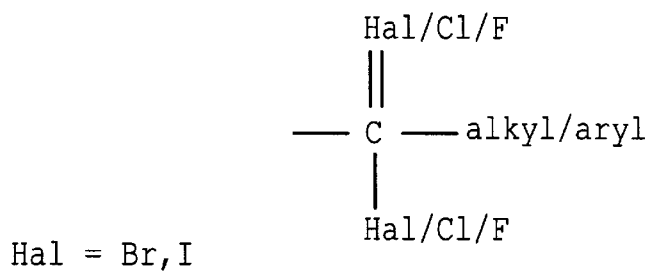

Hal = Br, I $H_2C\!=\!\!=\!\!—$ alkyl/aryl/substituted    (alkenes, vinyls)

Most suitable:

Methyliodide, methylbromide, ethyliodide, ethylbromide, propyliodide, propylbromide, butaneiodide, butanebromide, 1-iodopropane-2-one, 1-iodopropane-3-one, 1-bromopropane-2-one, 1-bromopropane-3-one, 1-iodo-2-fluoropropane, 1-iodo-2-chloropropane, 1-bromo-2-fluoropropane, 1-bromo-2-chloropropane, etc.

Fig. 13

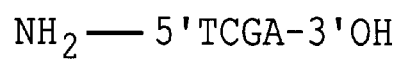
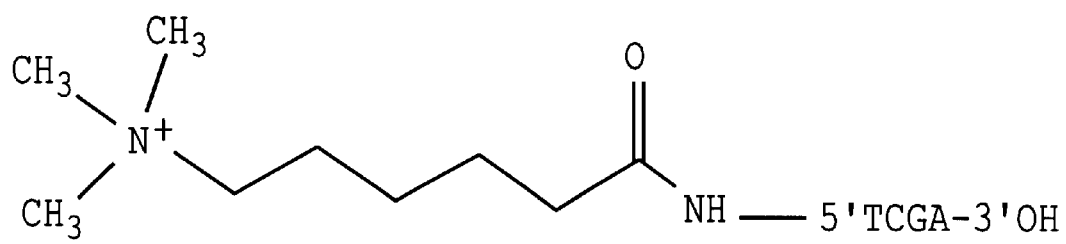
further chemical modification, i.e. full alkylation of phosphorothioate backbone
Fig. 14 one base extention product
starting material

5'OH-TCGATCGATCGA-3'OH 1) annealing to template
2) polymerase sequence ladder generation 5'OH-TCGATCGATCGATCGATCGA-3'NH$_2$
5'OH-TCGATCGATCGATCGATCGATCGA-3'NH$_2$
5'OH-TCGATCGATCGATCGATCGATCGATCGA-3'NH$_2$ charge tagging Fannigan
MAT LASERMAT: Matrix Assisted
Laser Desorption Mass Spectrometry
Spectrum printed at 17:41 Wed Feb 21 1996

Sample:       mix AGCT 1-12 in 6ATT 1:3000 dilution
Operator:     ivo
Account No:

Data File:    FILE NOT SAVED
Saved on:

No of shots:  12            Laser Aim: 2         Laser Power: 40
Polarity:     Positive      Acc. Voltage: 20041          Gain: 31mV
Calibration:  External      Mass 1: 0.0        Mass 2: 3496.9
PK. Detect:   TEST.CAL      A: -0.020          B/V: 0.530617

METHOD OF NUCLEIC ACID ANALYSIS

The present invention relates to a method of nucleic analysis, particularly to methods of DNA sequencing and detection of mutations.

The introduction of matrix assisted laser desorption ionization time-of-flight mass spectrometry (MALDI MS)[1] has opened new possibilities for the application of mass spectrometric analysis in molecular biology and, increasingly, in DNA analysis[2]. DNA has proven to be significantly more difficult to analyze by MALDI MS than peptides and proteins[3] due to very different mass ranges and the quantitative number of negative charges that have to be controlled for mass spectrometric analysis. The displacement of sodium by ammonium counter ions or very stringent desalting protocols improve the resolution significantly[4,5]. Using this improvement restriction enzyme digested fragments can be analysed by matrix assisted laser desorption[6]. Chemically synthesized methylphosphonate oligonucleotides which have an uncharged backbone show good definition by MALDI MS[7,8]. They were detected in positive ion mode while for the analysis of negatively charged oligonucleotides negative ion mode detection was preferable.

The partial alkylation of phosphorothioate containing oligonucleotides for selective chemical backbone cleavage has been described[9,10] and fluorescent reporter groups have been linked to oligonucleotides via phosphorothioate groups[11,12]. Work on the enzymatic incorporation of α-thio nucleotide triphosphates by DNA polymerases has been done for the development of alternative sequencing protocols[13,14].

To date, a simple and effective method of making nucleic acid, particularly DNA, more suitable for analysis by mass spectroscopy, especially when the said nucleic acid has been enzymatically synthesised, has not been devised.

A first aspect of the invention provides a method of analysing a nucleic acid by mass spectrometry comprising the steps of (1) providing a nucleic acid molecule containing no or up to ten negative charges and no or up to ten positive charges; (2) introducing the said nucleic acid molecule into a mass spectrometer; and (3) determining the mass of the said nucleic acid molecule, wherein when the nucleic acid molecule has no negative charges has greater than 17 sugar-sugar linkages and when the nucleic acid has a charge there are fewer charges than there are sugar-sugar linkages.

Preferably, when the nucleic acid has no negative charges it has >20 sugar-sugar linkages; more preferably >30 sugar-sugar linkages; and still more preferably >50 sugar-sugar linkages.

A second aspect of the invention provides a method of analysing a nucleic acid by mass spectrometry comprising the steps of (1) preparing a nucleic acid molecule comprising a negatively charged non-phosphate sugar-sugar linkage; (2) eliminating the charge from all, or up to all but ten, of the sugar-sugar linkages of the said nucleic acid molecule; (3) introducing the said nucleic acid molecule in which the charge has been wholly or partly eliminated as said into a mass spectrometer; and (4) determining the mass of the said nucleic acid molecule.

It will be appreciated that, although a mass spectrometer primarily determines the mass or mass/charge ratio of a molecule, it is feasible that the output of the mass spectrometer will indicate some other feature of the molecule being analysed such as its relative, rather than its absolute, mass. Therefore, by "determining the mass of the said nucleic acid molecule" we include determination of any physical characteristic derivable from the mass or relative mass of the said nucleic acid molecule.

It is preferred if the nucleic acid provided in the first aspect of the invention or prepared in the second aspect of the invention has no or one charge.

Having more than one charge on the molecule may be useful as it provides a way of increasing the mass range of the mass spectrometer as a mass/charge ratio is analysed. Mixed charges (wherein some parts of the molecule have a positive charge and some parts have a negative charge) can be used for selective neutralisation.

It is further preferred that the nucleic acid is DNA.

By "DNA" we mean a molecule with a sugar-linkage-sugar backbone wherein the sugar residue comprises a 2'-deoxyribose (and therefore includes a DNA chain terminated with a nucleoside comprising a 2',3'dideoxyribose moiety) and wherein, attached to the sugar residue at the 1 position is a base such as adenine (A), cytosine (C), guanine (G), thymidine (T), inosine (I), uridine (U) and the like. In normal DNA the linkage between sugar residues (the "sugar-sugar linkage") is a phosphate moiety which forms a diester with the said sugar residues. However, as will be clear from the specification we include in the term "nucleic acid" (and more particularly in the term DNA) molecules with non-phosphate linkages.

Thus, by "a negatively charged non-phosphate sugar-sugar linkage" we include a phosphorothioate linkage and a phosphoroselenoate linkage. A phosphorothioate linkage is most preferred.

By the term "nucleic acid" we also include molecules with non-natural base analogues; molecules in which the 2' and 3' positions of the pentose sugar are independently any of —H, —OH or —NH$_2$; and molecules in which an oxygen attached to the phosphorus atom but not in phosphodiester linkage is replaced by —SH, SeH, —BH$_2$, —NH$_2$, —PH$_3$, —F, —Cl, —CH$_3$, —OCH$_3$, —CN and —H. Such molecules are exemplified in FIG. 12. Replacement by —SH and —SeH is particularly preferred.

It is particularly preferred if the nucleic acid molecule has no phosphate sugar-sugar linkages.

It is also preferred if the nucleic acid molecule has any of one to ten phosphate sugar-sugar linkages; most preferably one.

It is most convenient if the mass spectrometry is matrix-assisted laser desorption ionization time-of-flight mass spectroscopy (MALDI MS) because the ionization conditions for the molecules are less severe than using other forms of mass spectroscopy, such as fast atom bombardment MS (FAB MS). Mass spectrometers, including MALDI mass spectrometers, are well known and are still improving in performance, particularly in mass resolution and sensitivity.

Conveniently, when the nucleic acid is uncharged or positively charged, the mass is determined in positive ion mode (PIM); similarly, when the nucleic acid is negatively charged, the mass is determined in negative ion mode. Indeed, when the nucleic acid molecule is uncharged no signal is detected in NIM.

The molecular masses of nucleic acid molecules as defined in the invention containing from two nucleoside moieties to around 1600 nucleoside moieties can be determined by mass spectroscopy and, as the spectrometers improve, it is envisaged that nucleic acid molecules of the invention of greater molecular mass could be used.

It is most preferred if the nucleic acid molecule whose mass is determined has between 2 and 500 nucleoside moieties; preferably between 5 and 300 nucleoside moieties; and more preferably between 10 and 200 nucleoside moieties.

Conveniently, the mass spectrometer is able to distinguish at least two nucleic acid molecules whose mass differs by the mass of a nucleoside moiety.

Although in some circumstances it may be useful to determine the molecular mass of a single nucleic acid species, it is preferred that a plurality of nucleic acid molecules with differing molecular mass are introduced into the mass spectrometer and the mass of at least one of the said molecules is determined.

As will be discussed in more detail below, it is particularly preferred if the nucleic acid is prepared using an enzymatic chain extension step. It is particularly preferred if a polymerase chain reaction or a chain terminating reagent is used in the preparation of the plurality of nucleic acids.

As is described in more detail below, a particularly preferred embodiment of the invention further comprises the step of determining a nucleotide sequence or detecting a mutation by comparing the masses or mass differences of the said plurality of nucleic acids molecules.

The provision of a nucleic acid molecule containing no or up to ten negative and no or up to ten positive charges, and the preparation of a nucleic acid molecule comprising a negatively charged non-phosphate sugar-sugar linkage, as well as nucleic acid molecules which are suitable for use in the methods, are described in the following aspects of the invention.

It is further preferred if certain salts are removed from the nucleic acid before introduction into the mass spectrometer. For example, NaI is produced in some of the methods described in the third aspect of the invention and it is convenient to remove this salt, and any buffer, from the nucleic acid. However, presence of $NH_4^+$ ions may increase the definition of the MS signal.

It is still further preferred if the 5' end of any nucleic acid is not a free hydroxyl. Preferably, as described below, it may be alkylated. It may also be phosphorylated (for example using ATP and T4 DNA kinase) to introduce, in some circumstances, a single phosphate (negative charge).

A third aspect of the invention provides a method of preparing a nucleic acid molecule containing no or up to ten negative charges and no or up to ten positive charges comprising the steps of (1) synthesising a nucleic acid with a phosphorothioate linkage or a phosphoroselenoate linkage between sugar residues, and (2) reacting the said nucleic acid with an alkylating agent so as to eliminate the charge on the said phosphorothioate linkage or said phosphoroselenoate linkage.

A particular advantage of this method is that uncharged, or substantially uncharged, nucleic acid can be made post-synthetically. A further advantage is that uncharged, or substantially uncharged, nucleic acid can be made which is longer than any uncharged nucleic acid that has been (or can be) made by de novo chemical synthesis.

In this third aspect of the invention a phosphorothioate linkage is most preferred.

Preferably the nucleic acid is DNA. Conveniently the nucleic acid molecule with a phosphorothioate linkage or with a phosphoroselenoate linkage is synthesised chemically, for example using solid phase phosphoramidite chemistry. A review of phosphorothioate-containing oligonucleotides and other nucleic acids is given in Eckstein & Gish[10]. Details of the synthesis and use of phosphorothioate- and phosphoroselenoate-containing oligonucleotides are given in References 10,23,24,25,26,27,28.

Alternatively, the nucleic acid molecule with a phosphorothioate linkage or with a phosphoroselenoate linkage is synthesised enzymatically. In this embodiment, an αS-dNTP or an αSe-dNTP is incorporated into a growing nucleic acid chain using a polymerase enzyme. At least the αS-dNTPs are readily commercially available for example from United States Biochemical Corporation, 26111 Miles Road, Cleveland, Ohio 44128, USA.

Polymerase enzymes are well known in the art of molecular biology and include *E. coli* DNA polymerase, T4 DNA polymerase and Taq DNA polymerase.

The Klenow fragment of *E. coli* DNA polymerase is a preferred enzyme and in this embodiment a nucleic acid template and a primer are used to synthesise the nucleic acid molecule. Conveniently, the primer is an oligonucleotide wherein each of the sugar-sugar linkages is either a phosphorothioate or a phosphoroselenoate linkage.

Suitably, primers may be modified (preferably at their 5' end) to include a moiety which will aid in purifying the product of primer extension. For example, biotin may be incorporated using well known methods and the primer (and any extension product) can be purified by binding to, and subsequent elution from, an immobilised streptavidin protein.

In a further embodiment, the primer contains regular phosphate sugar-sugar linkages and the extended product contains only phosphorothioate linkages. Alkylation of such a molecule with, for example, $ICH_2CH_2OH$ and subsequent heating to 95° C. will lead to the cleavage from the extended molecule of phosphate sugar-sugar linkage containing primer to leave a phosphorothioate-only linked extension product.

It is advantageous to include a single or up to ten positive charges in the primer. For example, the primer can be synthesised to include at its 5' end an amino group, preferably a secondary, tertiary or quaternary amino group that can be readily protonated to give a positive charge. In standard solid phase synthesis procedures, the 5' end of a primer (oligonucleotide) is a free hydroxyl group which can readily be reacted to provide an amino group.

Thus, it is preferred if step (1) of the method of the third aspect of the invention further comprises (a) synthesising said nucleic acid with a taggable group, said taggable group being capable of accepting a positive charge either directly or indirectly either before or after step (2), or (b) synthesising said nucleic acid with a precursor that comprises a positively charged moiety.

It is preferred if the taggable group accepts the positive charge before step (2).

By "directly" we mean that the taggable group itself is or can be made positively charged. By "indirectly" we mean that there is a linker (ie chemical spacer) between the taggable group and the positive charge.

Preferably, the method is used to introduce a single positive charge. As is described in more detail in Example 5, amino (or ammonium) groups, more particularly quaternary ammonium tags, may usefully be added to the nucleic acid that is to be analysed by mass-spectrometry. Suitably, the amino (or ammonium) group is added to a synthetic oligonucleotide (such as a primer) or to a PCR product either by a 5'-$NH_2$ link or by attaching a base containing an aliphatic $NH_2$ group to the 3'end of the DNA, for example by using the enzyme terminal transferase or directly by using a base for termination in a Sanger chain termination protocol which has an aliphatic $NH_2$ group by which the positively charged group can be added. In any case, the positively charged group (which is preferably a quaternary ammonium-containing compound) is then attached to the aliphatic —$NH_2$ group in the nucleic acid. Conveniently, the quaternary ammonium-containing compound comprises hydroxysuccinimidyl ester which reacts with aliphatic —$NH_2$ groups; preferably the compound is trimethyl ammonium hexyryl-N-hydroxysuccinimidyl ester (C5-NHS).

Suitably, the taggable group is any suitable group to which a positive charge may be added. Preferably, the taggable group is an aliphatic amino group, preferably a primary amino group.

It will be appreciated that the positively charged group may be attached using any suitable method.

The precursor of the nucleic acid may be any suitable precursor which comprises a positively-charged moiety. It is particularly preferred if the precursor is a dideoxynucleotide comprising a positively charged moiety and that the precursor is introduced into the nucleic acid using a polymerase. Conveniently, the dideoxynucleotide comprising a positively charged moiety is made from a nucleotide precursor that comprises an aliphatic amino group. Suitably, the dideoxynucleotide comprising a positively charged moiety is introduced into the nucleic acid in a Sanger sequencing reaction.

It is preferred if substantially all of the negative charges of the nucleic acid are removed and a single positive charge remains on the nucleic acid molecule.

It is advantageous to include a single or up to ten negative charges in the primer, the said negative charge being a charge that is not eliminated upon reaction with the said alkylating agent. Conveniently, a phosphate sugar-sugar linkage provides the negative charge which is not eliminated upon reaction with the said alkylating agent. A phosphate sugar-sugar linkage is readily incorporated into an oligonucleotide which otherwise has phosphorothioate or phosphoroselenoate sugar-sugar linkages using, for example, well known phosphoramidate chemistry.

In a particularly preferred embodiment each of the sugar-sugar linkages is either a phosphorothioate or a phosphoroselenoate linkage.

In one preferred embodiment, as well as an αS-dNTP or an αSe-dNTP being incorporated in a growing nucleic acid chain using a polymerase enzyme, a chain terminating a nucleotide is used in order to terminate the chain. Suitable chain terminating reagents include ddNTP, αS-ddNTP and αSe-ddNTP. The ddNTPs are readily commercially available from the usual suppliers of Sanger sequencing reagents. αSddNTPs are synthesised using the methods described in WO 93/23415 by reacting a 2',3'dideoxynucleoside with a mixture of thiophosphoryl chloride and pyridine at a temperature less than 130° C.

Thus, extension of a primer (which has each sugar-sugar linkage as a phosphorothioate or phosphoroselenoate linkage) using either αS-dNTP or αSe-dNTP (or a mixture thereof) in the presence of αS-ddNTP or αSe-ddNTP will lead to a plurality of nucleic acid molecules of varying sizes in which all of the sugar-sugar linkages are either a phosphorothioate linkage or a phosphoroselenoate linkage, each of said linkages being capable of reacting with an alkylating agent so as to eliminate the charge on the said linkage. Thus, in this embodiment a nucleic acid molecule with no charge is produced.

In a further preferred embodiment, the chain terminating nucleotide is ddNTP. In this embodiment, if the primer has each sugar-sugar linkage as a phosphorothioate or phosphoroselenoate linkage, and either αS-dNTP or αSe-dNTP is used to extend the nucleic acid chain, then incorporation of a ddNTP will yield a nucleic acid molecule wherein the 3'-most sugar-sugar linkage is a phosphate linkage, and all other sugar-sugar linkages are either phosphorothioate or phosphoroselenoate. Alkylation of this molecule so as to eliminate the charge on the phosphorothioate or phosphoroselenoate linkages will yield a molecule which has only a single, negative charge (at the single phosphate group).

It is particularly preferred if the alkylating agent reacts selectively, but substantially completely, with the phosphorothioate S atom or phosphoroselenoate Se atom. Thus, it is preferred if the alkylating agent does not react with the bases of nucleic acid or with any free hydroxyl groups of the nucleic acid.

Alternatively, but still preferably, the alkylating agent is one that reacts substantially completely with the phosphorothioate S atom or phosphoroselenoate Se atom and substantially completely with other reactive groups in the said nucleic acid, for example the bases of the nucleic acid or any free hydroxyl group of the nucleic acid.

In any case, it is preferred if the alkylating agent is substantially incapable of alkylating a phosphate group to form a stable nucleic acid.

By "alkylating agent" we include R-Hal wherein R is any of a primary, secondary or tertiary alkyl, alkenyl, —CO-alkyl, —CO-aryl, —CH(Hal/Cl/F) alkyl, —CH(Hal/Cl/F)-aryl, —C(Hal/Cl/F)(Hal/Cl/F)alkyl and —C(Hal/Cl/F)aryl and wherein Hal is independently Br or I and (Hal/Cl/F) is independently any of Hal or Cl or F.

By "aryl" we include phenyl, substituted phenyl, naphthyl and substituted naphthyl groups. Substitutions with an alkyl group or Hal or F or Cl are preferred.

Preferably the alkyl group is —$C_nH_{2n+1}$ wherein n is 1–20; more preferably n is 1–10; more preferably still n is 1–5.

Preferably the alkenyl group is —$C_nH_{2n-1}$ wherein n is 2–20; more preferably n is 2–10; more preferably still n is 2–5.

We also include alkenes and vinyls such as $H_2C$=CH-alkyl and $H_2C$=CH-aryl where the same alkyl and aryl groups as above are included.

This list is not exhaustive and we include all suitable alkylating agents.

Some of these molecules are shown in FIG. 13.

It is more preferred if the alkylating agent is any of methyliodide, methylbromide, ethyliodide, ethylbromide, propyliodide, propylbromide, butyliodide, butylbromide, 1-iodopropane-2-one, 1-iodopropane-3-one, 1-bromopropane-2-one, 1-bromopropane-3-one, 1-iodo-2-fluoropropane, 1-iodo-2-chloro-propane, 1-bromo-2-fluoropropane and 1-bromo-2-chloropropane.

It is further preferred if the alkylating agent is any of methyl iodide, ethyl iodide or propyl iodide, although, of these reagents propyl iodide reacts relatively slowly or is any of methyl bromide, ethyl bromide or propyl bromide.

Ethyl iodide is most preferred.

The alkyl bromides react more slowly than the equivalent alkyl iodides but are nevertheless useful. The alkyl bromides are less likely to alkylate any free 3'-OH or 5'-OH and this may be advantageous in a PCR and analysis by MALDI.

The size or shape of the alkylating agent is generally unimportant and so, as mentioned above alkylating agents with primary, secondary and tertiary alkyl chains, or with other substituents, may be used.

It is further preferred if any of the aforementioned compounds also include a proton acceptor group which can be protonated in the gas phase. Amino groups are preferred proton acceptor groups and so the alkylating groups of the invention include amino substituted alkyl and aryl groups. Thus, in this embodiment particularly preferred alkylating agents are $ICH_2CH_2NH_2$ and $ICH_2CH_2N(CH_3)_3^+ClO_4^-$.

When the alkylated nucleic acid molecule of this third aspect of the invention is analysed using the first or second aspects of the invention it is highly desirable that the alkylation is substantially complete and to the same extent for each molecule to be analysed. Thus, it is particularly preferred that substantially all phosphorothioate linkages or substantially all phosphoroselenoate linkages of substantially all of the nucleic acid molecules are so alkylated. It does not matter if other reactive groups of the nucleic acid molecule (such as the bases or hydroxyl groups) so long as that alkylation is substantially complete and to the same extent for each molecule to be analysed.

By "substantially complete" we mean that for any given molecule that >90% (but more preferably >95%; >99%; or >99.9%) of the sites available for alkylation with a particular alkylating agent (under given reaction conditions) are alkylated.

By "substantially all" we mean that for any given plurality of molecules >90% (but more preferably >95%; >99% or >99.9%) of the molecules are substantially completely alkylate (under given reaction conditions).

The extent of alkylation is important so that the masses or mass differences detected reflect differences in the number of nucleoside moieties in a nucleic acid molecule rather than the extent of alkylation.

It will be appreciated that using dideoxynucleotide chain terminating reagents in the synthesis of the DNA molecules of the third aspect of the invention, nested sets of DNA molecules can be synthesised wherein the sets comprise molecules that differ by a single nucleoside moiety (this, of course, is the principle of the Sanger sequencing method). As described in more detail in the Examples, the mass of each (or at least a substantial number) of the plurality of the nucleic acid molecules so generated can be determined according to the first or second aspect of the invention and, because the mass difference expected for each nucleoside moiety (comprising a base A, G, C or T) is known, the sequence of a nucleic acid can be determined.

Thus, the methods of the invention are useful in a quick DNA sequencing method which removes the need for gel electrophoresis of DNA molecules.

Similarly, the methods of the first and second aspects of the invention (particularly when using the alkylation method of the third aspect of the invention) can be used to determine mutations in a DNA sequence. Thus, for example, the mass of a given nucleic acid sequence can be readily calculated from the known molecular masses of bases, sugar and sugar-sugar linkages. If one or more bases is replaced by another base (as occurs in a mutation), the mass of the said given nucleic acid sequence will change in a predictable way. Thus, as is apparent (and is described in more details in the Examples) mutations can be readily detected.

In this embodiment of the invention it is particularly preferred if the nucleic acid molecule with a given sequence is produced by a polymerase chain reaction. The primers used in the PCR may be any of the primers described above (for example containing only phosphorothioate or phosphoroselenoate sugar-sugar linkages, or containing a single or up to ten phosphate linkages, the remaining linkages being phosphorothioate or phosphoroselenoate).

It is particularly preferred if the primers contain no phosphate linkage. The sequence of the primers are designed using well established principles so that the nucleic acid sequence of interest is amplified. Conveniently, αS-dNTPs or αSe-dNTPs are used and the resulting DNA molecule has only either phosphorothioate sugar-sugar linkages or phosphoroselenoate sugar-sugar linkages.

Preferably, the template DNA for the PCR reaction is derived from a patient, the said patient being a patient in which the presence or absence of a mutation is to be determined. There are many genetic diseases that are caused, at least in part, by well characterised DNA mutations. The method of this embodiment of the invention is particularly suited to the identification of the presence or absence of such a causative mutation including a mutation in any of the following genes: the cystic fibrosis transmembrane regulator (CFTR) gene which leads to cystic fibrosis; the Factor VIII or Factor IX genes which leads to haemophilia; $\alpha_1$-antitrypsin gene which leads to emphysema; the phenylalanine hydroxylase gene which leads to phenylketonuria; the ornithine transcarbamylase gene that leads to hyperammonaemia; the argininosuccinate synthetase gene which leads to citrullinaemia; the dystrophin gene which leads to muscular dystrophy; and in the β-globin gene, some of which lead to sickle cell, anaemia and some to thalassaemia.

Of course, the method is suited not only to point mutations but also to deletions, insertions and other types of mutation. Also, detection of differences in nucleotide sequences is useful in other areas such as DNA fingerprinting.

A fourth aspect of the invention provides a method of preparing a nucleic acid molecule containing no or up to ten negative charges comprising the steps of synthesising enzymatically the said nucleic acid using a dNTP uncharged at least at the α-phosphorus position.

Conveniently, the nucleic acid is synthesised using a primer and a polymerase.

It is preferred if the uncharged dNTP is a dNTP shown in FIG. 12 wherein $R_3$ is H and $R_1$ is any of $BH_2$, $CH_3$, $OCH_3$, F, —Cl or —H. $R_2$ is as given in FIG. 12 but is preferably OH.

As described in relation to the third aspect of the invention, various nucleic acid molecules are suitable as primers. It is preferred if the primer is an oligonucleotide wherein each of the sugar-sugar linkages is either uncharged or is capable of having its charge eliminated. Linkages which are capable of having their charge eliminated include a phosphorothioate linkage and a phosphoroselenoate linkage. As in the third aspect of the invention, the primer may be positively charged. The primer may also comprise a phosphate as a sugar-sugar linkage.

A fifth aspect of the invention provides an uncharged nucleic acid molecule has greater than 17 sugar-sugar linkages. Preferably, the nucleic acid molecule has >20; more preferably >30 and still more preferably >50 sugar-sugar linkages. Such molecules are readily synthesised using, for example, the third and fourth aspects of the invention.

A sixth aspect of the invention provides a nucleic acid molecule with no or up to ten negative charges wherein at least one sugar-sugar linkage comprises an alkylated phosphorothioate moiety or an alkylated phosphoroselenoate moiety. Such molecules are readily synthesised using, for example, the third aspect of the invention.

Preferably each of the sugar-sugar linkages is either an alkylated phosphorothioate linkage or an alkylated phosphoroselenoate linkage.

In one embodiment, at least one base of the molecule is alkylated. In a preferred embodiment each of the said bases, if it can be alkylated, is alkylated.

Preferably, the phosphorothioate linkage or phosphoroselenoate linkage is alkylated with a residue of any of the alkylating agents described in the third aspect of the invention.

It is particularly preferred if the said alkylated linkage is an alkylated phosphorothioate linkage. It is further preferred if the linkage is alkylated with a methyl, ethyl or propyl residue.

A seventh aspect of the invention provides an uncharged nucleic acid molecule comprising a phosphoro sugar-sugar linkage wherein in each phosphoro linkage the phosphorous atom is substituted with any one of —$BH_2$, —$OCH_3$, —F, —Cl, or —H.

An eighth aspect of the invention provides a nucleic acid molecule containing one to ten phosphate sugar-sugar linkages wherein all other sugar-sugar linkages are uncharged. Preferably the nucleic acid comprises at least 20 nucleoside residues; more preferably at least 50 nucleoside residues.

A further aspect of the invention provides a nucleic acid with one or up to ten positive charges wherein the sugar-sugar linkages are uncharged. Preferably, each sugar-sugar linkage is either an, alkylated phosphorothioate moiety or an alkylated phosphoroselenoate moiety. More preferably the nucleic acid has a single positive charge. The nucleic acids of this aspect of the invention can be synthesised using a method of the third aspect of the invention.

A ninth aspect of the invention provides a use of an alkylating agent which reacts selectively, but substantially completely, with a phosphorothioate S atom or a phosphoroselenoate Se atom.

Preferably, the alkylating agent is one that reacts substantially completely with the phosphorothioate S atom or phosphoroselenoate Se atom and substantially completely with other reactive groups in the said nucleic acid molecule.

In a preferred embodiment the alkylating agent is as defined in the third aspect of the invention. It is particularly preferred if the alkylating agent is methyl iodide, ethyl iodide or propyl iodide.

Preferably the use to which the alkylating agent is put is to alkylate a nucleic acid wherein each of the sugar-sugar linkages is either a phosphorothioate or a phosphoroselenoate linkage; or wherein up to ten sugar-sugar linkages is a phosphate linkage and each of the remaining said linkages is either a phosphorothioate or a phosphoroselenoate linkage.

Tenth, eleventh, twelfth and thirteenth aspects of the invention provide a method of suppressing gene expression in a cell comprising administering to the cell an antisense nucleic acid wherein the antisense nucleic acid is a nucleic acid obtainable by the third and fourth aspects of the invention or a nucleic acid of the fifth, sixth, seventh or eighth aspects of the invention; use of any of the said nucleic acids as an antisense nucleic acid; a said nucleic acid for use in medicine; and a pharmaceutical formulation comprising a said nucleic acid and a pharmaceutically acceptable carrier.

It is particularly preferred that the nucleic acid is the nucleic acid obtainable by the method of the third aspect of the invention, in particular by synthesising a nucleic acid with a phosphorothioate linkage between sugar residues and reacting the said nucleic acid with an alkylating agent so as to eliminate the charge on the said phosphorothioate linkage.

Antisense nucleic acids (more usually referred to as antisense oligonucleotides although we do not use this to indicate a size limitation) are single-stranded nucleic acid, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. Thus, the nucleic acid molecules of the invention may be able to specifically bind double-stranded DNA via recognition of major groove hydrogen binding sites.

By binding to the target nucleic acid, the above oligonucleotides can inhibit the function of the target nucleic acid. This is, for example, a result of blocking the transcription, processing, poly(A) addition. replication, translation, or promoting inhibitory mechanisms of the cells, such as promoting RNA degradations.

The antisense oligonucleotide of the invention can be used to selectively suppress certain cellular functions. For example, in oncogenic transformed cells, oligonucleotides complementary to the oncogene suppress its expression. An antisense oligonucleotide has previously been shown by others to inhibit c-myc protein expression in a human promyelocytic leukaemia cell line, HL60, which over expresses the c-myc proto-oncogene. The antisense oligonucleotide used was complementary to regions of the c-myc mRNA. A nucleic acid of the present invention with the same base sequence is expected to work in the same way with an advantage of being substantially nuclease resistant and facile to make.

Antisense oligonucleotides can also be used to inhibit replication and expression of nucleic acid foreign to the host cells. The antisense oligonucleotides are prepared as described above and then introduced into cells, for example by microinjection or uptake from the cell culture medium into the cells, or by administration to a patient. Antisense oligonucleotides can also be used to inhibit viral replication or expression in cell culture for example, Rous sarcoma virus, vesicular stomatitis virus, herpes simplex virus type 1, simian virus and influenza virus. Oligonucleotides complementary to the poly(A) signal are effective; also effective are those targeted at the 5' end of the RNA, particularly the cap and 5' untranslated region, next to the primer binding site and at the primer binding site. The cap, 5' untranslated region, and poly(A) signal lie within the sequence repeated at the ends of retrovirus RNA (R region) and the oligonucleotides complementary to these may bind twice to the RNA.

The antisense oligonucleotide may be any useful antisense oligonucleotide, for example an oligonucleotide complementary to DNA or RNA specifically forming part of a gene for the mutant ras protein, the mutant p53 protein, the BCR-ABL fused mRNA characteristic of the Philadelphia chromosome in chronic myeloid leukaemia (CML) and acute lymphocytic leukaemia (ALL), or an HIV (human immunodeficiency virus) protein, for example the HIV gag, pol, env or sor gene products. By "specifically", we mean that the complementary DNA or RNA does not normally appear in a normal (non-tumour or non-virally-infected) cell. Further targets for the antisense DNA/RNA include the HIV tRNA (Lys) primer binding site, mRNA splice donor or acceptor sites, the poly A region and the initiator codons of the HIV genes mentioned above.

Conveniently, the antisense nucleic acids (or oligonucleotides) have between 10 and 500 bases, more preferably 15 to 200 bases, most preferably 20 to 100 bases.

In accordance with the invention, the inherent binding specificity of antisense oligonucleotides characteristic of base pairing is enhanced by limiting the availability of the antisense compound to its intend locus in vivo, permitting lower dosages to be used and minimizing systemic effects. Thus, oligonucleotides are applied locally to achieve the desired effect. The concentration of the oligonucleotides at the desired locus is much higher than if the oligonucleotides were administered systemically, and the therapeutic effect can be achieved using a significantly lower total amount.

The local high concentration of oligonucleotides enhances penetration of the targeted cells and effectively blocks translation of the target nucleic acid sequences.

The oligonucleotides can be delivered to the locus by any means appropriate for localized administration of a drug. For example, a solution of the oligonucleotides can be injected directly to the site or can be delivered by infusion using an infusion pump. The oligonucleotides also can be incorporated into an implantable device which when placed at the desired site, permits the oligonucleotides to be released into the surrounding locus.

The oligonucleotides are most preferably administered via a hydrogel material. The hydrogel is noninflammatory and biodegradable. Many such materials now are known, including those made from natural and synthetic polymers. In a preferred embodiment, the method exploits a hydrogel which is liquid below body temperature but gels to form a shape-retaining semisolid hydrogel at or near body temperature. Preferred hydrogel are polymers of ethylene oxide-propylene oxide repeating units. The properties of the polymer are dependent on the molecular weight of the polymer and the relative percentage of polyethylene oxide and polypropylene oxide in the polymer. Preferred hydrogels contain from about 10 to about 80% by weight ethylene oxide and from about 20 to about 90% by weight propylene oxide. A particularly preferred hydrogel contains about 70% polyethylene oxide and 30% polypropylene oxide. Hydrogels which can be used are available, for example, from BASF Corp., Parsippany, N.J., under the tradename Pluronic®.

In this embodiment, the hydrogel is cooled to a liquid state and the oligonucleotides are admixed into the liquid to a concentration of about 1 mg oligonucleotide per gram of hydrogel. The resulting mixture then is applied onto the surface to be treated, for example by spraying or painting during surgery or using a catheter or endoscopic procedures. As the polymer warms, it solidifies to form a gel, and the oligonucleotides diffuse out of the gel into the surrounding cells over a period of time defined by the exact composition of the gel.

The oligonucleotides can be administered by means of other implants that are commercially available or described in the scientific literature, including liposomes, microcapsules and implantable devices. For example, implants made of biodegradable materials such as polyanhydrides, polyorthoesters, polylactic acid and polyglycolic acid and copolymers thereof, collagen, and protein polymers, or non-biodegradable materials such as ethylenevinyl acetate (EVAc), polyvinyl acetate, ethylene vinyl alcohol, and derivatives thereof can be used to locally deliver the oligonucleotides. The oligonucleotides can be incorporated into the material as it is polymerized or solidified, using melt or solvent evaporation techniques, or mechanically mixed with the material. In one embodiment, the oligonucleotides are mixed into or applied onto coatings for implantable devices such as dextran coated silica beads, stents, or catheters.

The dose of oligonucleotides is dependent on the size of the oligonucleotides and the purpose for which is it administered. In general, the range is calculated based on the surface area of tissue to be treated. The effective dose of oligonucleotide is somewhat dependent on the length and chemical composition of the oligonucleotide but is generally in the range of about 30 to 3000 μg per square centimeter of tissue surface area.

The oligonucleotides may be administered to the patient systemically for both therapeutic and prophylactic purposes. The oligonucleotides may be administered by any effective method, for example, parenterally (eg intravenously, subcutaneously, intramuscularly) or by oral, nasal or other means which permit the oligonucleotides to access and circulate in the patient's bloodstream. Oligonucleotides administered systemically preferably are given in addition to locally administered oligonucleotides, but also have utility in the absence of local administration. A dosage in the range of from about 0.1 to about 10 grams per administration to an adult human generally will be effective for this purpose.

A still further aspect of the invention provides a method of analysing a nucleic acid by mass spectrometry comprising the steps of (1) providing a nucleic acid molecule comprising a positively-charged moiety; (2) introducing the said nucleic acid molecule into a mass spectrometer; and (3) determining the mass of the said nucleic acid. Preferably the sugar-sugar linkages of the nucleic acid are substantially all phosphate sugar-sugar linkages. As is shown in Example 5, there are advantages to including a positively charged moiety into a nucleic acid whether or not the negative charges of the sugar-sugar linkages are eliminated or not.

A further aspect of the invention provides a method of preparing a nucleic acid comprising a positively-charged moiety comprising synthesising a nucleic acid with a taggable group, said taggable group being capable of accepting a positive charge either directly or indirectly. Preferably, the sugar-sugar linkages of the nucleic acid are substantially all phosphate sugar-sugar linkages.

By "directly" we mean that the taggable group itself is or can be made positively charged. By "indirectly" we mean that there is a linker (ie chemical spacer) between the taggable group and the positive charge.

Preferably, the method is used to introduce a single positive charge. As is described in more detail in Example 5, amino (or ammonium) groups, more particularly quaternary ammonium tags, may usefully be added to the nucleic acid that is to be analysed by mass-spectrometry. Suitably, the amino (or ammonium) group is added to a synthetic oligonucleotide (such as a primer) or to a PCR product either by a 5'-$NH_2$ link or by attaching a base containing an aliphatic $NH_2$ group to the 3'end of the DNA, for example by using the enzyme terminal transferase or directly by using a base for termination in a Sanger chain termination protocol which has an aliphatic $NH_2$ group by which the positively charged group can be added. In any case, the positively charged group (which is preferably a quaternary ammonium-containing compound) is then attached to the aliphatic —$NH_2$ group in the nucleic acid. Conveniently, the quaternary ammonium-containing compound comprises hydroxysuccinimidyl ester which reacts with aliphatic —$NH_2$ groups; preferably the compound is trimethyl ammonium hexyryl-N-hydroxysuccinimidyl ester (C5-NHS).

Suitably, the taggable group is any suitable group to which a positive charge may be added. Preferably, the taggable group is an aliphatic amino group, preferably a primary amino group.

It will be appreciated that the positively charged group may be attached using any suitable method.

The following abbreviations are used through the specification: PT=phosphorothioate; MALDI=matrix assisted laser desorption ionization; MALDI MS=matrix assisted laser desorption ionization time-of-flight mass spectrometry; NIM=negative ion mode; PIM=positive ion mode; DMF=dimethylformamide, SA=sinapinic acid, 234-THA=2,3,4-trihydroxyacetophenone, 246-THA=2,4,6-trihydroxyacetophenone, Tris/DMF=3 mM Tris/HCl in 90% DMF pH=8.6

The invention will now be described with reference to the following Examples and Figures wherein:

FIG. 1 is a diagram representing alkylation of phosphorothioate oligonucleotides. R'=CH$_3$I, C$_2$H$_5$I, C$_3$H$_7$I.

FIG. 2 is an autoradiograph of the alkylation reaction of a $^{32}$P-end labelled phosphorothioate oligonucleotide (all phosphorothioate M13mp18 forward primer, 17-mer) with C$_2$H$_5$I in 3 mM Tris/HCl 90% dimethylformamide at 55° C. (first series: a=before addition of alkylating agent, b=after addition of alkylating agent, before heating, c=15 min heating, d=30 min heating, e=1 h heating, f=2 h heating; second series: g=before addition of alkylating agent, h=after addition of alkylating agent, before heating, i=15 min heating, j=after second addition of alkylating agent and 30 min heating, k=after third addition of alkylating agent and 1 h heating, l=after fourth addition of alkylating agent and 2 h heating). The increasing extent of alkylation can be seen by the appearance of bands with lower mobility. Only some unchanged material (fully alkylated) can be seen in the well since fixing the gel involves soaking in 10% acetic acid which probably leads to removal of the material from the well. The two remaining bands visible in the second series are due to the incomplete alkylation of the phosphate label.

FIG. 3 shows the time course of the alkylation reaction followed by MALDI MS. The alkylation of phosphorothioate 5'hexyl-AGCT with C$_2$H$_5$I in 3 mM Tris/HCl in 90% dimethylformamide at 55° C. is monitored in a (SA, NIM, peak detected at 1484 Da), b (234-THA, NIM, 1484 Da), c (246-THA, NIM, 1484 Da), d (SA, PIM, 1514 and 1542 Da), e (234-THA, PIM, 1514 and 1542 Da) and f (246-THA, PIM, 1514 and 1542 Da). Timepoint 1=after addition of alkylating agent, 2=30 min heating, 3=1 h heating (more alkylating agent was added after each sampling). After 1 h NIM came down to baseline and PIM signals decreased slightly due to dilution by added alkylating agent.

FIG. 4 shows MALDI mass spectra of the alkylation product of phosphorothioate 5'hexyl-AGCT with C$_2$H$_5$I in 3 mM Tris/HCl in 90% dimethylformamide after 3 h at 55° C. recorded in positive ion mode (A) and negative ion mode (B). Sinapinic acid was used as matrix. Full alkylation of the 3'-OH groups was achieved in the shown spectra. Often incomplete alkylation of 3'-OH is observed and manifests itself as a double peak, the two peaks differing by the mass of the alkyl group.

FIG. 5 shows a MALDI mass spectrum of a mixture of ethylated phosphorothioate HO-TTT, HO-AGCT and HO-T$_{10}$. Alkylation was done with C$_2$H$_5$I in 3 mM Tris/HCl 90% dimethylformamide at 55° C. for 2 h. Sinapinic acid was used as matrix and the spectrum recorded in positive ion mode. Masses detected are 967, 1336, 3408. The resolution number m/Δm is 160 for the lower peaks and 120 for the 10-mer.

FIG. 6 is a model for the gas phase behaviour of oligonucleotides during matrix assisted laser desorption ionization. 1) After desorption of the matrix a plume containing a mixture charged, neutral, hot and cold molecules start interacting with each other. 2) Collisions with the native oligonucleotide lead to the release of sodium cations. The negative charges on the oligonucleotides are immediately neutralized by collisions with compounds with high gas phase acidity. 3) The plume reduces due to molecules that have been accelerated out of it. Collisions with the oligonucleotides still lead to the release of sodium but saturation of the residual negative charge on the sugar phosphate backbone of the oligonucleotide no longer takes place. 4) The oligonucleotide with the negative charge is accelerated out of the plume.

FIG. 7 shows the masses of various alkylated phosphorothioate oligonucleotides.

FIGS. 10A–10H show a diagrammatic representation of a DNA sequencing reaction using the methods of the present invention. The oligonucleotides shown in FIGS. 10A–10H are given in the Sequence Listing as SEQ ID NOs:5–34.

FIGS. 11A–11C show a diagrammatic representation of a polymerase chain reaction using the methods of the invention. The oligonucleotides shown in FIGS. 11A–11C are given in the Sequence Listing as SEQ ID NOs 44 and 45.

FIGS. 12A and 12B show the chemical structures of various nucleotides contemplated for use in various aspects of the invention.

FIG. 13 shows the chemical structures of various alkylating agents for use in various aspects of the invention.

FIG. 14 is a schematic of chemical attachment of a charge tag to the 5' end of an oligonucleotide with subsequent further modification of the oligonucleotide backbone (ie backbone alkylation). The same chemistry can also be done using an aliphatic amino group attached to the 3'end of an oligonucleotide.

Figure 15:

FIG. 15 describes the terminal transfer of 3'NH$_2$-ddTTP to an oligonucleotide as a handle for chemical attachment of a charge tag. A $^{32}$P-labelled oligonucleotide is treated with 3'transferase and 3'NH$_2$-ddTTP tested as a substrate (lane 2). As control the untreated oligonucleotide is used (lane 1) and the oligonucleotide using dATP as a control substrate (lane 3). In the case of 3'NH$_2$-ddTTP the shift due to one additional base can be observed while use of dATP as substrate leads to a ladder of products with increasing length.

Figure 16:
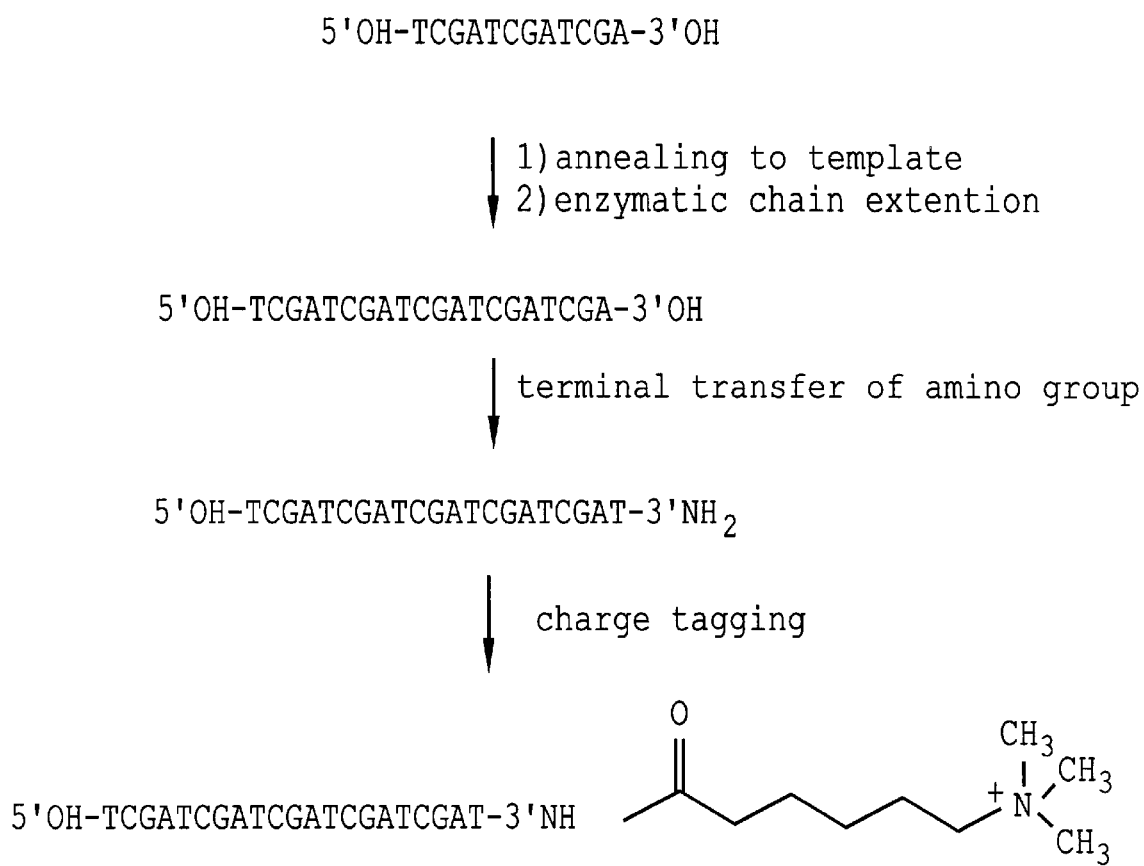

FIG. 16 is a schematic of a terminal transferase reaction to attach a group, that can be used as an anchor for charge tagging, to a piece of DNA. The oligonucleotides shown in FIG. 16 are in the sequence listing as SEQ ID No 35 and 36.

Figure 17:
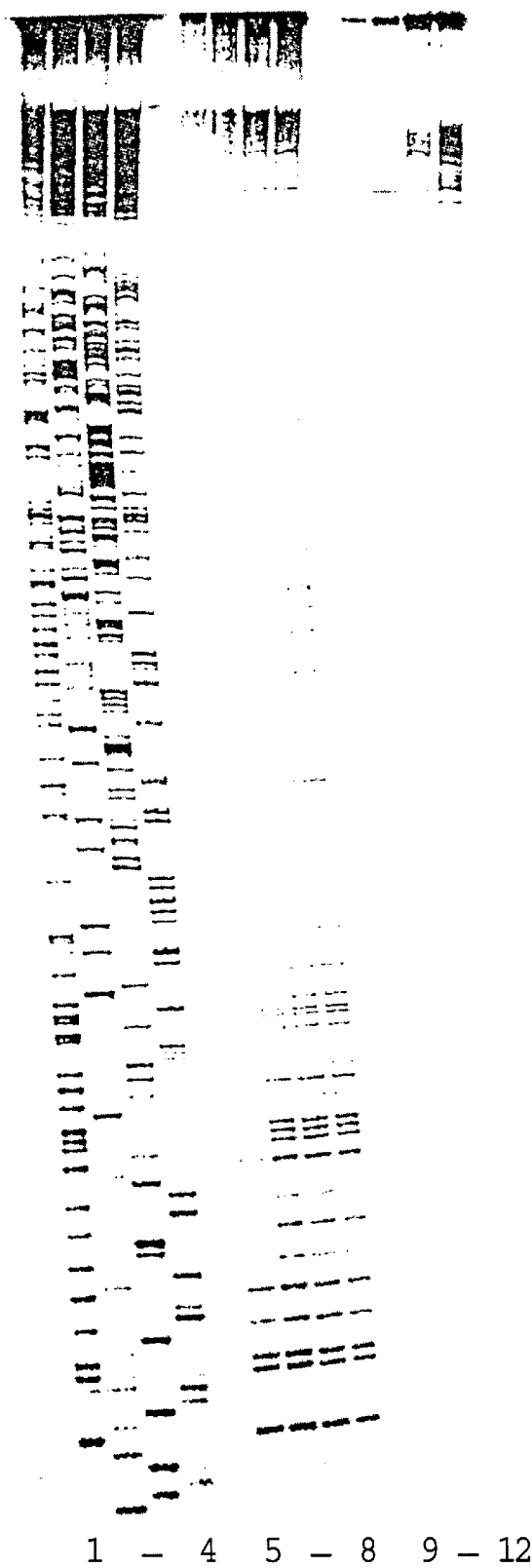

FIG. 17 describes the termination of a sequencing reaction using native 3'NH$_2$-ddTTP and charge tagged 3'NH$_2$-ddTTP. A standard sequencing reaction is run alongside the titration of the terminators (lanes 1–4, loaded TCGA). 3'NH$_2$-ddTTP specifically terminates at the same positions as ddTTP terminates (titrated in lanes 5–8). The final concentration gives an even incorporation pattern while at higher concentration the products are terminated short. Charge tagged 3'NH$_2$-ddTTP also shows specific termination (titrated in lanes 9–12).

Figure 18:
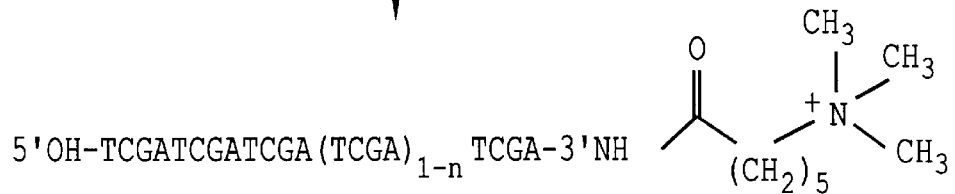

FIG. 18 is a schematic of a sequencing reaction using a 3'NH$_2$-ddNTP base for termination. The charge tag group is subsequently attached to the terminating group. The oligonucleotides shown in FIG. 18 are in the sequence listing as SEQ ID No 35, 37 and 38.

Figure 19A:
Figure 19B:
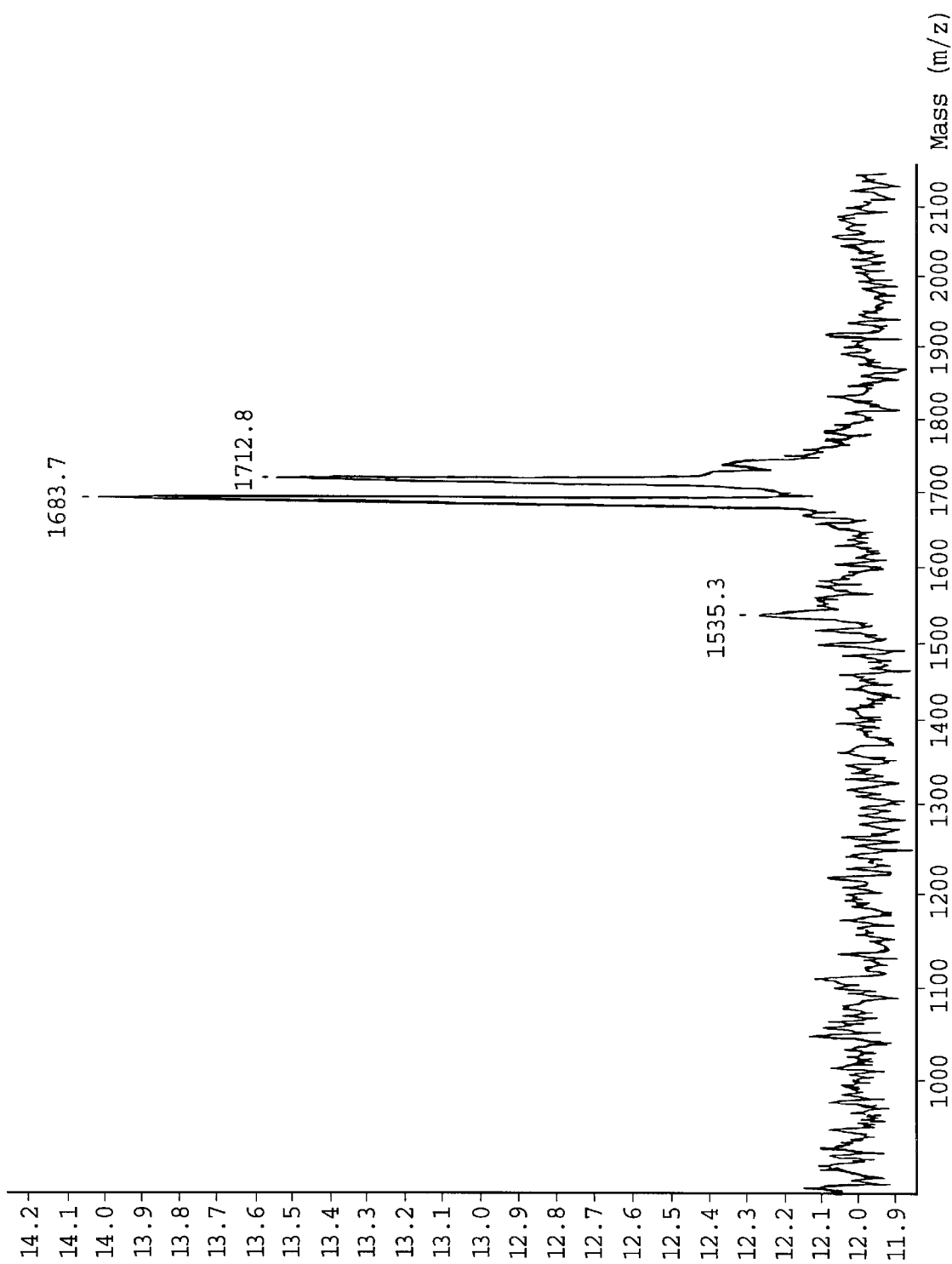

FIGS. 19A and 19B show a MALDI mass spectrometry race of an equimolar mixture of twelve differently modified and unmodified 4-mer (samples 1–12 of Table 1 of Example 5). 30 fmoles of each oligonucleotide is used for the sample preparation. The matrix used is 6-aza-2-thiothymidine. Only the charge tagged and backbone neutralised oligonucleotides 8 and 10 are observed.

EXAMPLE 1
Alkylation of Phosphorothioate Linked Oligonucleotides and Detection by Mass-spectrometry
Materials and Methods The phosphorothioate deoxyoligonucleotides listed below were synthesized by an in-house oligonucleotide synthesis service by standard phosphoramidite chemistry: HO-CCC, HO-TTT, HO-AAA, HO-GGG, HO-AGCT, HO-TTTTTTTTT (SEQ ID No 1), HO-TCGATCGATCGA (SEQ ID No 2), M13mp18 forward sequencing primer HO-GTAAAACGACGGCCAGT (SEQ ID No 3). Regular HO-TTTTTTTTT (SEQ ID No 1) was also synthesized.

Phosphorothioate 5'hexyl-dAGCT was custom synthesized by Oswel DNA Service, University of Edinburgh (Edinburgh EH9 3JJ, UK) using standard phosphoramidite chemistry. A hexyl building block ($C_6H_{13}$) was coupled to the 5'end also via a PT link.

Deoxyadenosine 5'-α-thiotriphosphate (Sp-isomer, dATP-α-S), deoxycytidine 5'-α-thiotriphosphate (Sp-isomer, dCTP-α-S), deoxyguanosine 5'-α-thiotriphosphate (Sp-isomer, dGTP-α-S), thymidine 5'-α-thiotriphosphate (Sp-isomer, dTTP-α-S) were purchased from Amersham International (Little Chalfont, UK). $CH_3I$, $C_2H_5I$, $C_3H_7I$, 2,3,4-trihydroxyacetophenone, 2,4,6-trihydroxyacetophenone, sinapinic acid and L-tartaric acid diammonium salt were purchased from Aldrich (Gillingham, UK).

5'End-labelling ($^{32}P$) of PT oligonucleotides was done with T4 polynucleotide kinase according to the protocol of Mundi et al[15]. T4 polynucleotide kinase was purchased from New England Biolabs (Bishop's Stortford, UK) and γ-$^{32}P$ dATP from Amersham International (Little Chalfont, UK).

Alkylation of phosphorothioate linked oligonucleotides. The thio specific alkylation of PT oligonucleotides (FIG. 1) was evaluated in different solvent systems (data not shown) with a series of alkylating agents ($CH_3I$, $C_2H_5I$, $C_3H_7I$). Efficient alkylation was achieved in 10% v/v 30 mM Tris/HCl pH 8.0+90% dimethylformamide, final pH=8.6 (Tris/DMF). Reactions were done in closed 0.5 ml Eppendorf tubes. 5 μl of Tris/DMF, 1 μl of the PT oligonucleotide (~1 mM, 1 nmole) and 1 μl of the alkylating agent (~10 nmoles) were mixed and placed in a water bath at 55° C. 1 μl samples were taken at different time intervals and analyzed by MALDI MS or gel electrophoresis. The reaction time for efficient alkylation was $CH_3I<C_2H_5I<C_3H_7I$. $CH_3I$ was more difficult to handle than the other alkylating agents due to its low boiling point of 43° C. and some of it might have been lost during sampling, although sampling was done at room temperature. With $C_2H_5I$ the addition of alkylating agent (0.5–1 μl) after each sampling led to full alkylation of the PT backbone in less than 1 h at 55° C. The reaction time could still be further reduced by raising the reaction temperature. A control reaction under the same conditions (pH, temperature) but without DMF did not result in any alkylation of the PT groups.

Gel assay. Oligonucleotides were separated on 20 cm×0.4 mm 15% polyacrylamide gels containing 8 M urea. They were run for 1–2 hours at 40 W, fixed for 20 minutes in 10% acetic acid, dried and x-ray film (Fuji RX) exposed to them for 5 hours.

Matrix Assisted Laser Desorption Ionization time-of-flight mass spectrometry (MALDI MS). Equivalent amounts of crude reaction mixture and 2% solutions of sinapinic acid (SA) in 50% aqueous acetonitrile (usually 1 μl each) were mixed. 0.5 μl (containing ~35 pmoles of product) was spotted onto the target slide and air dried. Solvents and volatile alkylating agents ($CH_3I$, $C_2H_5I$, $C_3H_7I$) evaporated upon formation of the matrix while the product was embedded in the matrix. Starting materials and products were also analyzed using a 2% 2,3,4-trihydroxyacetophenone (234-THA) or 2,4,6-trihydroxyacetophenone (246-THA) matrix in 50% aqueous ethanol with 100 mM L-tartaric acid diammonium salt added according to the method of Pieles et al[5]. Mass spectra were recorded on a Finnigan MAT Laser-Mat 2000 time-of-flight mass spectrometer, essentially described by Mock et al[16]. Although the mass spectrometer was not internally calibrated the resolution was usually better than ±2 Da in the mass range below 4000 Da which was sufficient for these experiments.

Results

Figure 1:
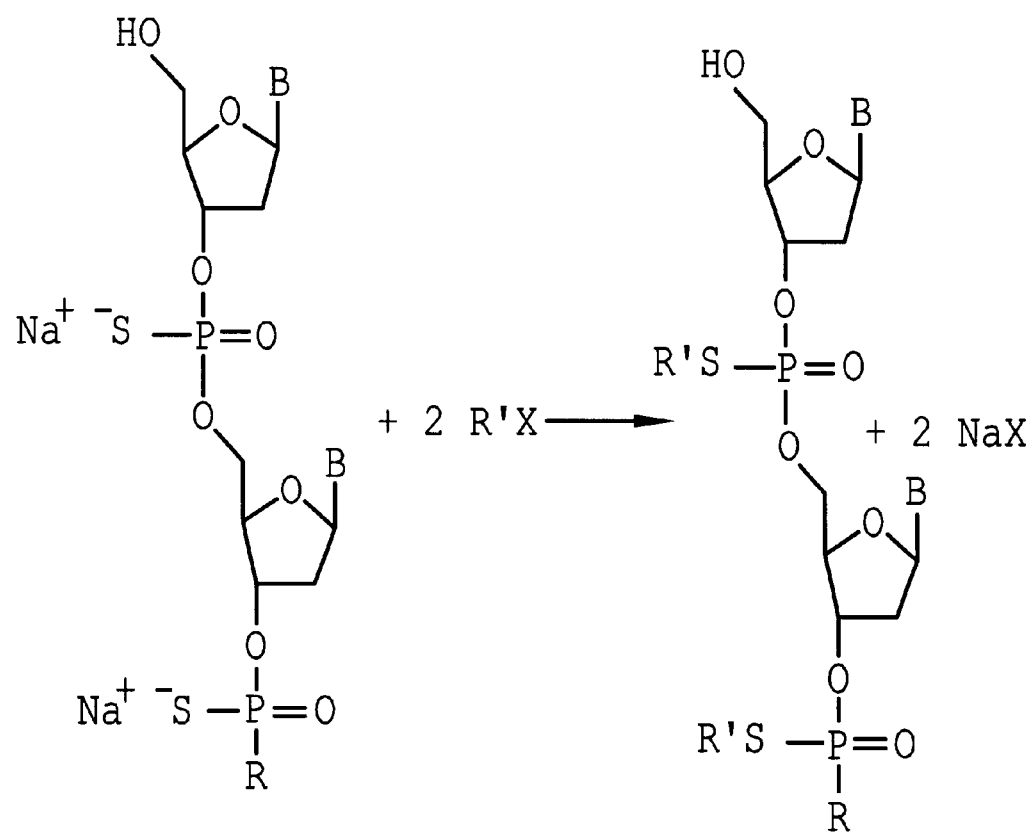
Figure 2:
Figure 3:
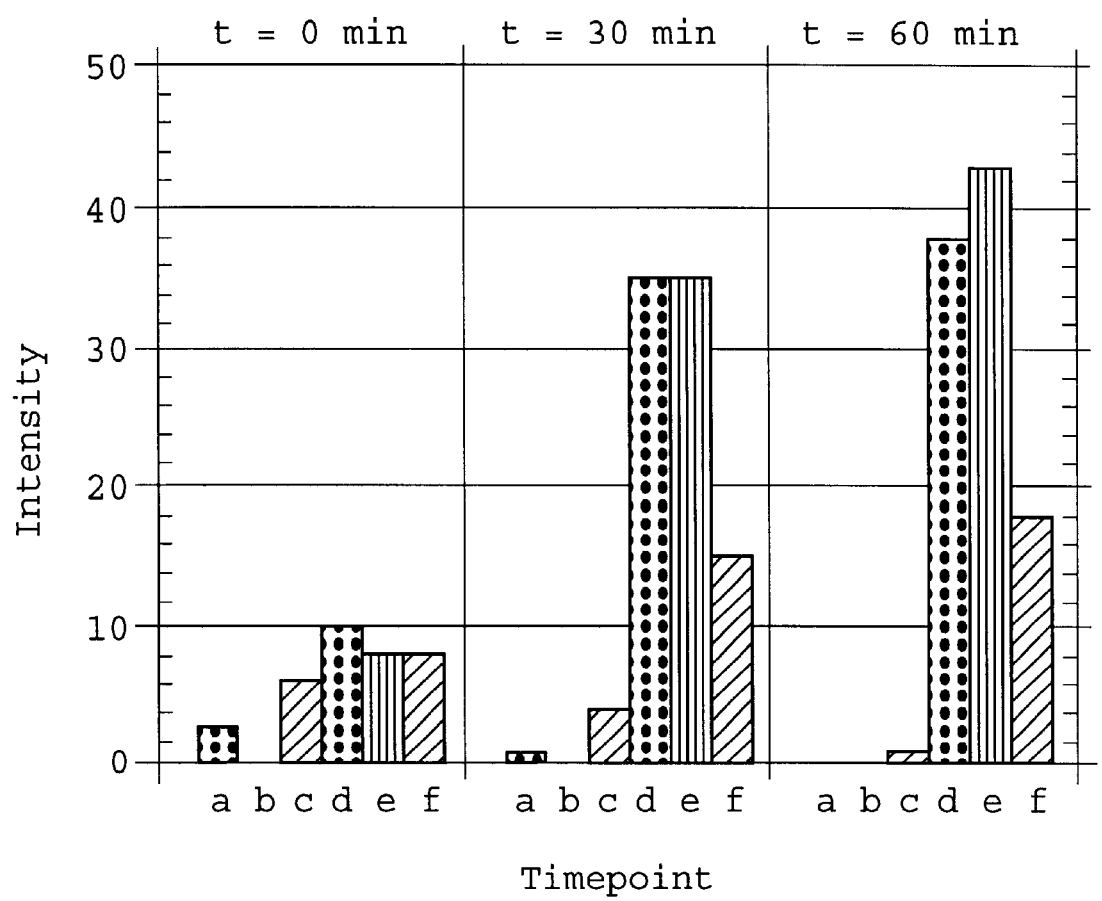

The alkylation of phosphorothioate oligonucleotides. Phosphorothioate oligonucleotides were alkylated very efficiently using a 90% DMF solution containing 3 mM Tris/HCl pH, 8.0, final pH 8.6 at 55° C. (FIG. 1). $C_2H_5I$ was found to be a very appropriate alkylating agent for this purpose. Under these conditions the reaction of $C_2H_5I$ with PT oligonucleotides was complete within 1 h. The alkylation rate seems to be independent of the length of the oligonucleotide (FIGS. 2 and 3).

Analysis of alkylated phosphorothioate oligonucleotides by gel electrophoresis. In addition to MALDI MS analysis (described below), the alkylation products were studied by gel electrophoresis using $^{32}P$ 5'-end labelled PT oligonucleotides. Removal of charges from the backbone which corresponds to alkylation reactions were monitored by reduced mobility of the oligonucleotide in gel electrophoresis. Individual alkylation steps can be seen as a ladder of oligonucleotides with decreasing number of charges. FIG. 2 shows the time course of the alkylation of a $^{32}P$-end labelled PT 17-mer (M13mp18 forward sequencing primer) with $C_2H_5I$ in Tris/DMF. The effect of adding $C_2H_5I$ after each time the reaction is sampled is clearly visible. Fully alkylated material can not migrate into the gel due to its lack of charge and therefore will largely be lost during the work up of the gel (fixing in 10% acetic acid). The inefficiency of alkylation of the phosphate label (estimated to be roughly 40%) results in two residual bands on the gel. However, alkylation products that are not associated with the alkylation of the PT groups, and therefore do not correspond to the removal of charges, could not be detected in this assay but by MALDI MS. A control alkylation of the same PT 17-mer at pH=8.6 in protic solvent did not lead to the formation of backbone alkylation products.

Figure 4A:
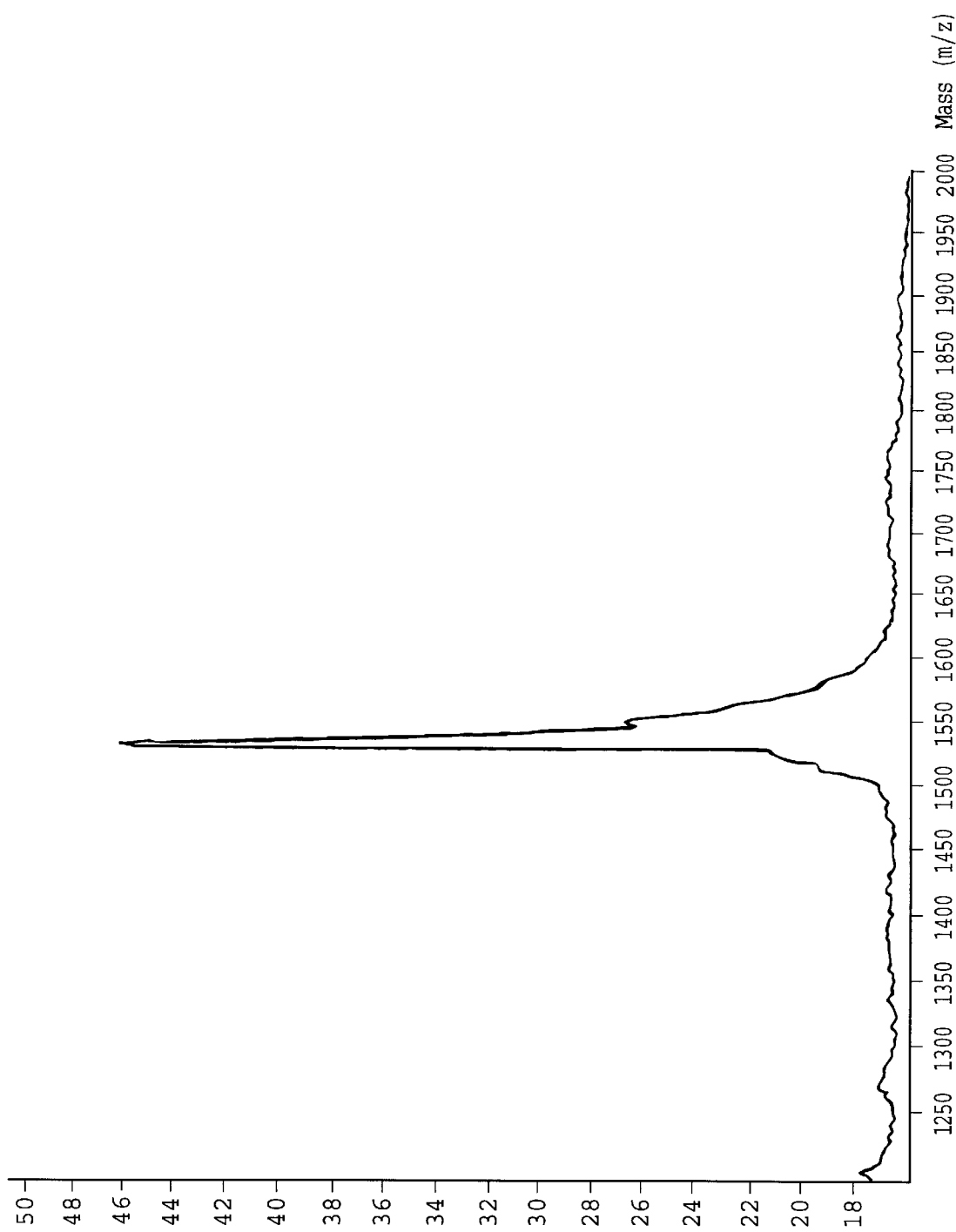
Figure 4B:
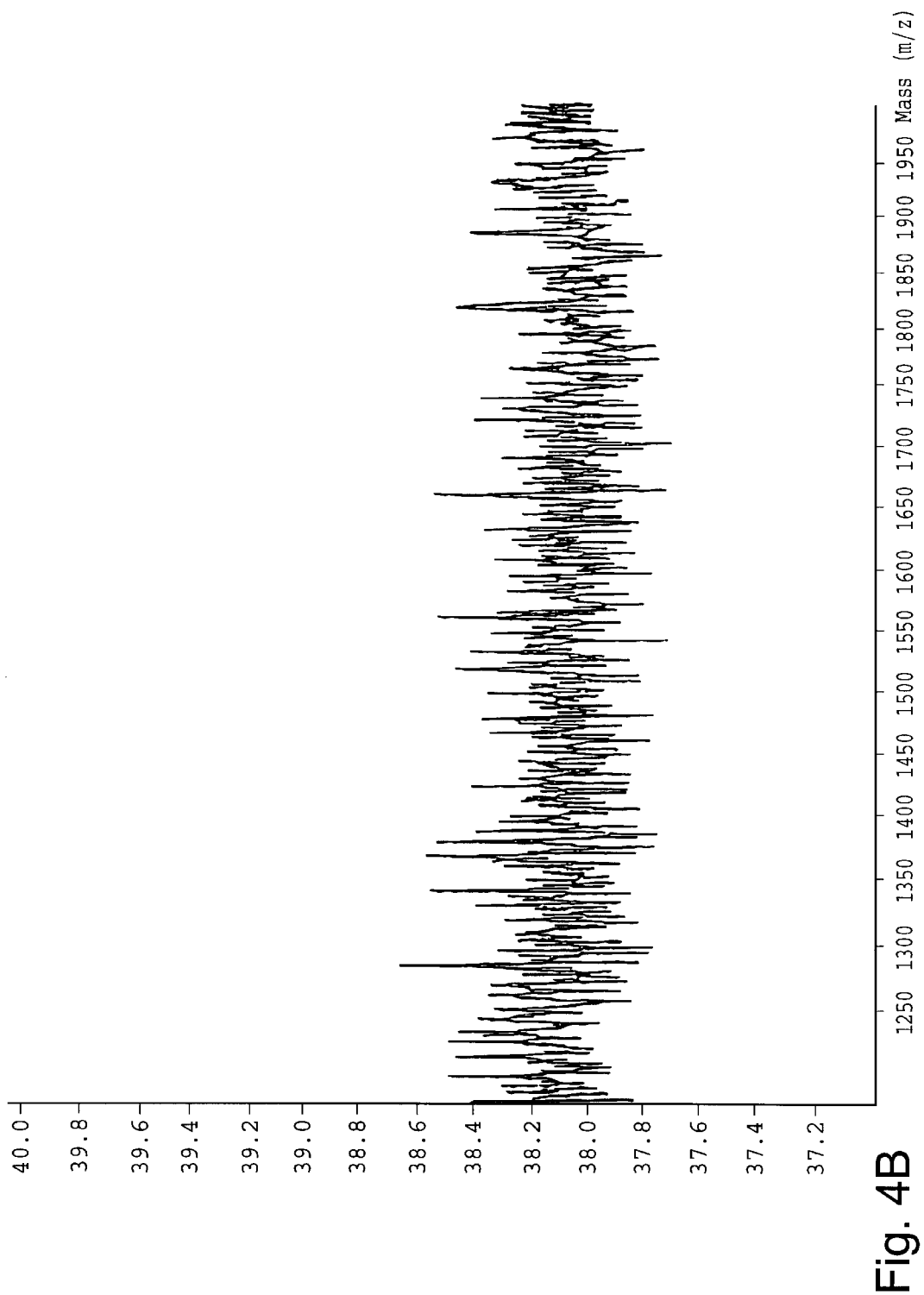

Comparison of MALDI MS detection in positive and negative ion mode. The kinetics of alkylation of PT oligonucleotides were followed by MALDI MS both in positive ion mode (PIM) and negative ion mode (NIM). During the reaction the different PT alkylation steps could be observed in NIM with exception of the fully alkylated PT oligonucleotide. Upon completion of the alkylation of the PT groups no signals at all could be detected in NIM. The fully alkylated PT oligonucleotide could be analyzed in PIM with improvingly excellent resolution during the reaction (FIG. 4).

The selectivity of the alkylation of PT oligonucleotides was studied on the set of 3-mers. HO-TTT, HO-CCC, HO-GGG, HO-AAA, and HO-TCGA (all PT linked) were alkylated in Tris/DMF and analyzed by MALDI MS using sinapinic acid, 2,3,4-trihydroxyacetophenone and 2,4,6-trihydroxyacetophenone as matrices (FIG. 7). Spectra were recorded in PIM and NIM as described above. Alkylation with $CH_3I$ was very efficient. Products with masses corresponding to the oligonucleotides with up to six methyl groups were observed which indicates base alkylation. Higher alkylation products were found with purine 3-mers indicating that this alkylating procedure leads to the alkylation of adenine and guanine while cytosine and thymine remained unreacted. For $CH_3I$ no solvent conditions were found under which the alkylation was selective for the PT groups. Propylation with $C_3H_7I$ was found to be comparatively slow. It is conceivable that a protocol with higher temperatures could be worked out as the propylation was selective for PT and no base alkylation was observed. $C_2H_5I$ was very practical under these conditions. It did not alkylate any of the four bases, but efficiently ethylated the phosphorothioate backbone. The higher boiling point of $C_2H_5I$ than $CH_3I$ made its handling significantly easier. The addition of alkylating agent after sampling helped drive the backbone alkylation to completion without leading to base alkylation. Due to the small reaction volumes it is probable that some of the alkylating agent is lost during sampling. It was found that the 5'- and 3'-hydroxy groups were susceptible to alkylation by $CH_3I$, $C_2H_5I$ and to a lesser extent by $C_3H_7I$ although these alkylations were not quantitative.

Details of the results shown in FIG. 7 are given in the following paragraph.

Measured and calculated masses of phosphorothioate oligonucleotides and their alkylation products formed in 3 mM Tris/HCl in 90% DMF at pH 8.6. MALDI MS analysis of the native phosphorothioate oligonucleotides, that gave the masses of the free acids, were carried out in 2,3,4-trihydroxyacetophenone matrix after addition of L-tartaric acid diammonium salt. The alkylation products were analyzed using sinapinic acid as matrix. [–] indicates that no signal could be detected, while empty positions were not attempted. With $CH_3I$ multiple higher methylation was found with purine bases and assigned to the alkylation of bases. With $C_2H_5I$ negative ion mode analysis showed a product during the reactions with the mass of the free acid of the phosphorothioate oligonucleotide plus the number of PT groups –1 times ethylated. The endpoint of alkylation was determined by the disappearance of negative ion mode signal. In positive ion mode products with a mass of the free acid of the oligonucleotide plus the number of phosphorothioate groups +1 or +2 times ethylated were observed. This indicates that one or both of the end —OH groups were alkylated in addition to all phosphorothioate groups. Alkylation with $C_3H_7I$ was slow in comparison. Only products of the mass of the phosphorothioate oligonucleotide with no more than the number of phosphorothioate groups +1 times alkylated were observed.

In order to prevent alkylation of the 5'-end oligonucleotides were designed where the 5'-OH is replaced by a 5'-hexyl chain linked to the oligonucleotide via a PT group. FIG. 3 shows the time course of the ethylation of PT 5'-hexyl-AGCT, monitored in PIM and NIM in three different matrices (SA, 234-THA and 246-THA). In all three matrices the appearance of signals at 1514 Da and 1542 Da (4 and 5 times alkylated starting material) was detected in PIM. In NIM a signal at 1484 Da (3 times alklated starting material) was detected in SA and 246-THA matrix. This signal disappeared in the course of the reaction. Using 234-THA and NIM no signal could be detected during the reaction. FIG. 4 shows the PIM and NIM spectra after completion of the alkylation using SA. In this experiment the 3'-OH was found to be completely alkylated although often a double peak with masses corresponding to 4× and 5× alkylated starting material was observed in PIM indicating that the 3'-OH alkylation is not quantitative. However it was considered obsolete to constrict the alkylation of the 3'-OH as in the Sanger sequencing chemistry the terminating dideoxy bases lack this group anyway.

Ethylation products of longer PT oligonucleotides could be detected by MALDI MS. HO-$T_{10}$ (PT linked) gave a well resolved signal that corresponded to eleven alkylations in PIM using SA as matrix. No corresponding signal was detected in NIM after completion of the alkylation which indicates optimal conditions for alkylation. The control alkylation of a regular HO-$T_{10}$ in Tris/DMF gave a product that corresponded in mass to the 4 times ethylated starting material this indicates about 40% efficiency of alkylation of regular phosphate groups under these conditions. It could only be detected in NIM. PT HO-$(TCGA)_3$ could be ethylated to completion under the same conditions. The signal detected in PIM was very symmetrical, well resolved and corresponded to the starting oligonucleotide ethylated 12 times. During the reaction the decreasing signal of the 10 times ethylated intermediate could be detected in NIM. Products with fewer than 10 alkylations could never be resolved during the alkylation indicating that they are either never abundant enough for detection or that higher alkylation products are more easily detected by MALDI MS due to their homogeneity.

Throughout signals of complete alkylation products detected in PIM were stronger than the signals of starting materials. The ratio strongly depended on the matrix.

Salts, like NaI, which is a side product of the alkylation reaction, and buffers, were not removed. This might lead to a certain degree of suppression for larger oligonucleotides but could not be observed with the instrument used.

Figure 5:
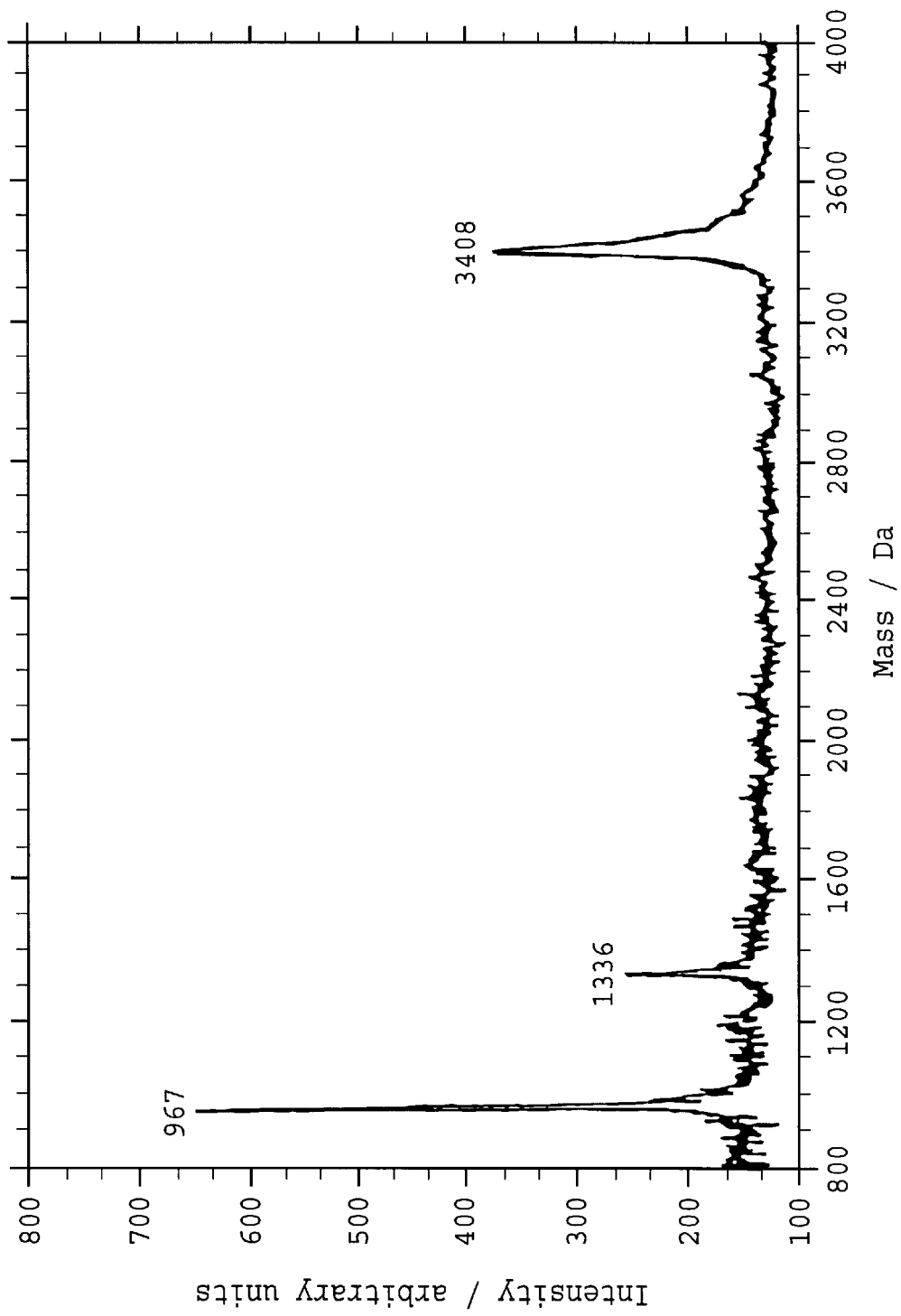

A mixture of ethylated HO-TTT, HO-AGCT and HO-$T_{10}$ (all PT linked) was analysed by MALDI MS using sinapinic acid as a matrix (FIG. 5). Excellent separation and definition of signals was observed. The instrument specific resolution number slightly decreased to m/$\Delta$m=120 for the 10-mer. Interestingly the analysis of a mixture of starting material with an equal concentration ratio of the three oligonucleotides, analyzed in 246-THA (with the addition of 100 mM L-tartaric acid diammonium salt) in NIM, yielded a different intensity ratio. The alkylated mixture gave HO-TTT>HO-$T_{10}$>HO-AGCT while the starting material gave HO-AGCT>HO-TTT>>HO-$T_{10}$. Clearly there is a significant difference in the mode of ionization which might account for this observation.

Discussion

Using 3-mers simplifies the MS analysis of alkylation products as there are only 3 distinguishable alkylation positions with different multiplicities and detectability in alternate ion modes (2 bridge phosphorothioate groups, 2 end OH groups and 3 bases). Base and end alkylation can be analyzed in negative ion mode while complete backbone alkylation products can be detected in positive ion mode. The alkylation of the end groups was studied using end modified mixed 4-mers (PT 5'hexyl-AGCT). We found that signal definition could be improved by this substitution. Alkylation at different positions leads to an overall higher number of alkylations and detection of larger products. For example (FIG. 7) in the exhaustive alkylation of PT HO-AAA with $CH_3I$ the addition of six alkyl groups was detected in PIM (2 bridge PT groups, 2/3 bases and 2/1 end OH groups). This indicates that the methylation of the PT groups runs to completion but bases are also methylated under these conditions.

For $C_2H_5I$ the highest number of alkyl groups added to the PT 3-mer was 4. The reaction could not be driven any further. Usually mixtures of 3 and 4 times ethylated 3-mers were found in positive ion mode without a corresponding negative ion mode signal. While no base ethylation takes place the reaction with the phosphorothioate groups is quantitative but there is a degree of end alkylation.

Figure 6:
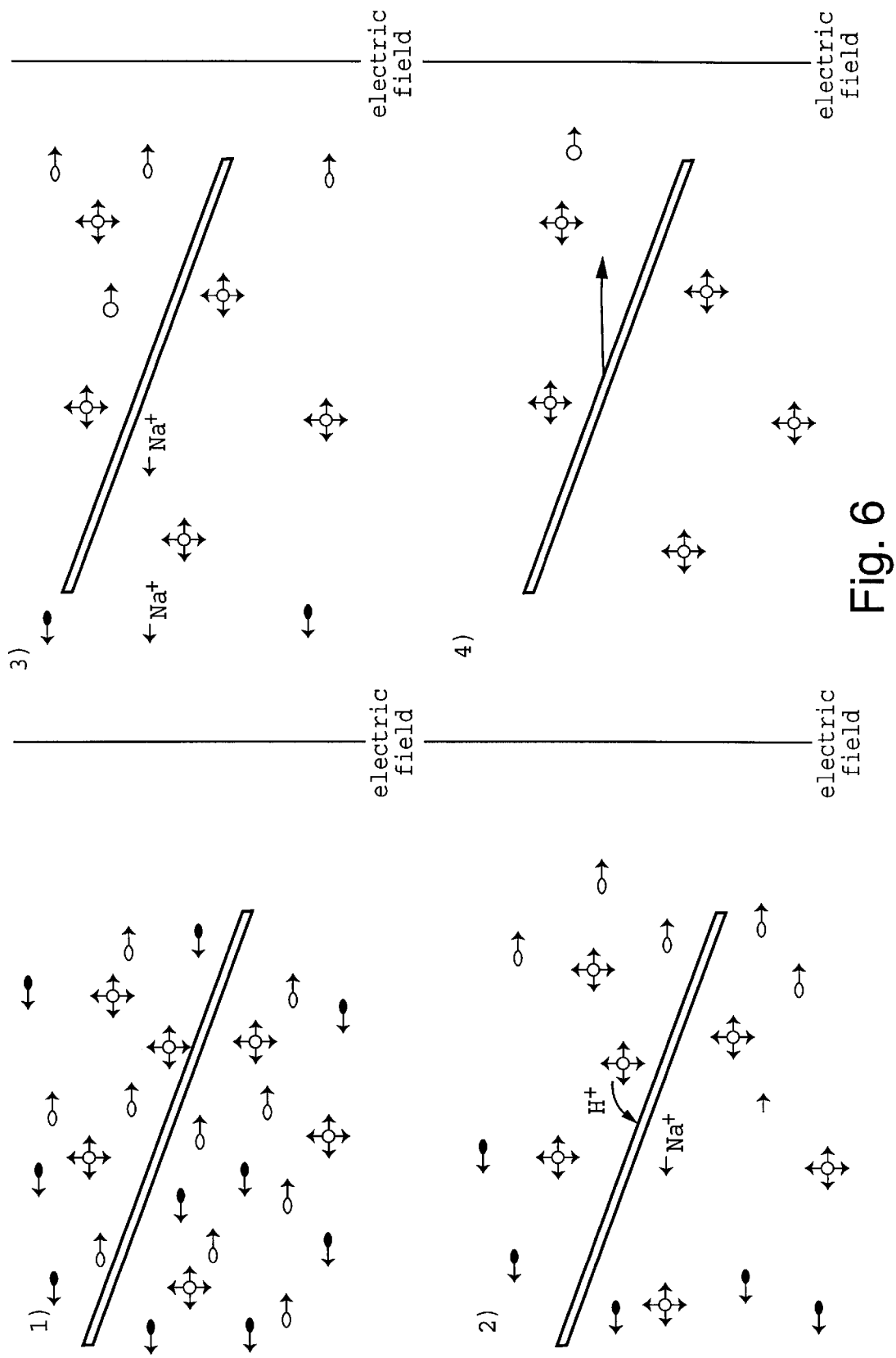

One of the main problems of MALDI MS of oligonucleotides is the decrease in resolution for increasing length of the oligonucleotide[17,18]. Both in this study and before[7,8] it has been found that non ionic oligonucleotides give good definition for signal even in mixtures. We have tried to visualize the process of MALDI of oligonucleotides and have developed the following model for plausibility (FIG. 6):

1) Desorption: the laser induced desorption process produces a situation where hot and charged species originating from the matrix material diverge interspersed with cold overall charge neutral oligonucleotides. Charge separation starts taking place due to the electric field that the molecules in the plume are exposed to. The oligonucleotides stay associated with their counter ions.
2) Ion exchange: collisions of hot matrix material with the analyte lead to the displacement of $Na^+$ from the sugar-phosphate backbone. The negative charge of the phosphate is saturated by molecules with high gas phase acidity in a concerted event. The possibility for the dissipation of energy of matrix fragments decreases as the particle density decreases.
3) Ionization: the ionization process that gives a charge to the oligonucleotide, required for the acceleration, takes place when the concentration of strong gas phase acids drops below a critical concentration and the probability for a concerted event gets small. In a sense ionization could be viewed as a failure of the ion exchange process.
4) Acceleration: the charged oligonucleotide is accelerated towards the detector.

With increasing length of an oligonucleotide the number of ion exchange events increases. Incomplete exchange results in broadening of the signal. Often $Na^+$ adducts have been observed although usually the predominant peak detected corresponded to the mass of the free acid. The amount of matrix material consumed increases linearly with the concentration of bases and might therefore reach a level of saturation where no further ion exchanges can take place. This might also explain why mixtures of oligonucleotides show poorer signals for the larger oligonucleotides while the same large oligonucleotides analyzed on their own show better resolution[17]. The resolution/definition is a function of the overall concentration of analyte and therefore a function of the number of ionic positions in an oligonucleotide. In a mixture of oligonucleotides a large oligonucleotide requiring more collisions will feel the effect of an exhausting matrix most strongly. A logical solution would be to lower the concentration of oligonucleotide analyte material but, of course, this decreases the detectability. With analyte to matrix ratios of 1:100[19] very efficient exchange would have to be achieved in order to obtain reasonable signal with longer oligonucleotides (>20 bases). Higher ratios in favour of the matrix (1:10$^4$) have been used and this definitely helps to improve the probability of a successful quantitative exchange[20]. The time frame in which the ion exchange takes place is of significance for the resolution. If the ion exchange is rapid and the generation of an ion thereafter efficient one can expect good resolution. With time passing after the vaporization process the probability of collisions decreases exponentially. It has been found that the addition of $NH_4+$ significantly increases the definition of a signal[13]. This is in accordance with our model in that $NH_4^+$ ions upon displacement from the sugar-phosphate backbone, themselves act as acids due to their high gas phase acidity and provide the protons back to the oligonucleotide. If ionization processes were predominant over ion exchange processes one would expect to see larger amounts of doubly and triply charged species. Usually predominantly singly charged species are observed. On the other hand if exchange events were highly more efficient than ionization events within the model described one would obtain the charge neutral free acid of an oligonucleotide and that would most likely be detected in positive ion mode after base protonation as the gas phase acidity of the matrix has to be high for rapid exchanges.

The gas phase interaction of molecules and fragment molecules is of vital importance to the analysis of oligonucleotides by MALDI. By selective alkylation which leads to complete removal of negative charges from the PT oligonucleotide backbone, we manage to reduce the number of gas phase events between vaporization and detection. The advantage of low numbers of events required is evident. The simple alkylation protocol allows bridging the gap between ionic and non ionic DNA easily and gives access to using the mass spectrometer in positive ion mode. Only a single gas phase ionization event is required for the analysis of backbone alkylated DNA compared to the n−1 (n being the number of charges of the oligonucleotide) ion exchange reactions and one ionization process required for the analysis of a regular oligonucleotide in negative ion mode.

Recently Nordhoff et al have found that N-glycosidic bonds are more prone to break in DNA than RNA during MALDI resulting in the loss of a base[4]. They propose that the 2'-OH group in RNA stabilizes the N-glycosidic bond while in DNA the phosphate proton is transferred to the base which leads to the breakage of the N-glycosidic bond. Our alkylation protocol leads to a completely new arrangement of groups on an oligonucleotide backbone and a significant decrease in the acidity of the backbone. No breakage of the alkylated backbone was observed in our MALDI MS analysis.

EXAMPLE 2

Enzymatic Generation of Phosphorothioate DNA

A Sanger type approach can be used for sequencing DNA by MALDI because no large "waste" fragments are generated like in a chemical degradation (eg Maxam and Gilbert type) DNA sequencing approach which might obscure a MALDI analysis. Purification of extended single strand DNA from proteins, residual trinucleotides and salts can be done by facile precipitation procedures or other purification techniques such as magnetic bead purification are applied[21].

We have integrated an α-S-dideoxy cytidine triphosphate thus enzymatically generating a fully phosphorothioate oligonucleotide.

Materials and Methods

5'biotin-CAGGCATGCAAGCTTGGCACTGGC-CGTCGTTTTACAACGT (SEQ ID No 4), 40-mer of the M13 sequence contains the reverse complementary sequence for the M13 forward sequencing primer (HO-GTAAAACGACGGCCAGT (SEQ ID No 3) (all phosphorothioate links)). These oligonucleotides were synthesized by an in house oligonucleotide synthesis service.

5'Hexyl phosphorothioate oligonucleotides were custom synthesized by Oswel DNA Service, University of Edinburgh (Edinburgh EH9 3JJ, UK) hexyl-GTAAAACGACGGCCAGT (SEQ ID No 3) (all phosphorothioate links) M13 forward sequencing primer.

Deoxyadenosine 5'-α-thiotriphosphate (Sp-isomer), deoxycytidine 5'-α-thiotriphosphate (Sp-isomer), deoxyguanosine 5'-α-thiotriphosphate (Sp-isomer), thymidine 5'-α-thiotriphosphate (Sp-isomer) were purchased from Amersham (Little Chalfont, UK). Dideoxycytidine 5'-α- thiotriphosphate (1:1 mix of R and S isomers) was used. This was kindly supplied by Amersham International, Little Chalfont, UK and was synthesised by the method described in WO 93/23415. $CH_3I$, $C_2H_5I$, $C_3H_7I$ were purchased from Aldrich (Gillingham, UK).

5'End-labelling ($^{32}P$) of fully phosphorothioate linked oligonucleotides was done with T4 polynucleotide kinase according to the protocol of Mundi et al[15].

Use of α-$^{35}$S-ATP incorporation for labelling in primer extension reactions with Klenow fragment was done according to regular radioactive sequencing protocols described earlier[22]. Oligonucleotides smaller than 40 bases were separated on 20 cm×0.5 mm 15% acrylamide gels containing 8 M urea. They were run for 1–2 hours at 500 V after an initial run in at 200 V. Larger oligonucleotides were separated on 50 cm×0.5 mm 6% acrylamide gels containing 8 M urea and are run for 4 h at 2000 V.

Figure 8:
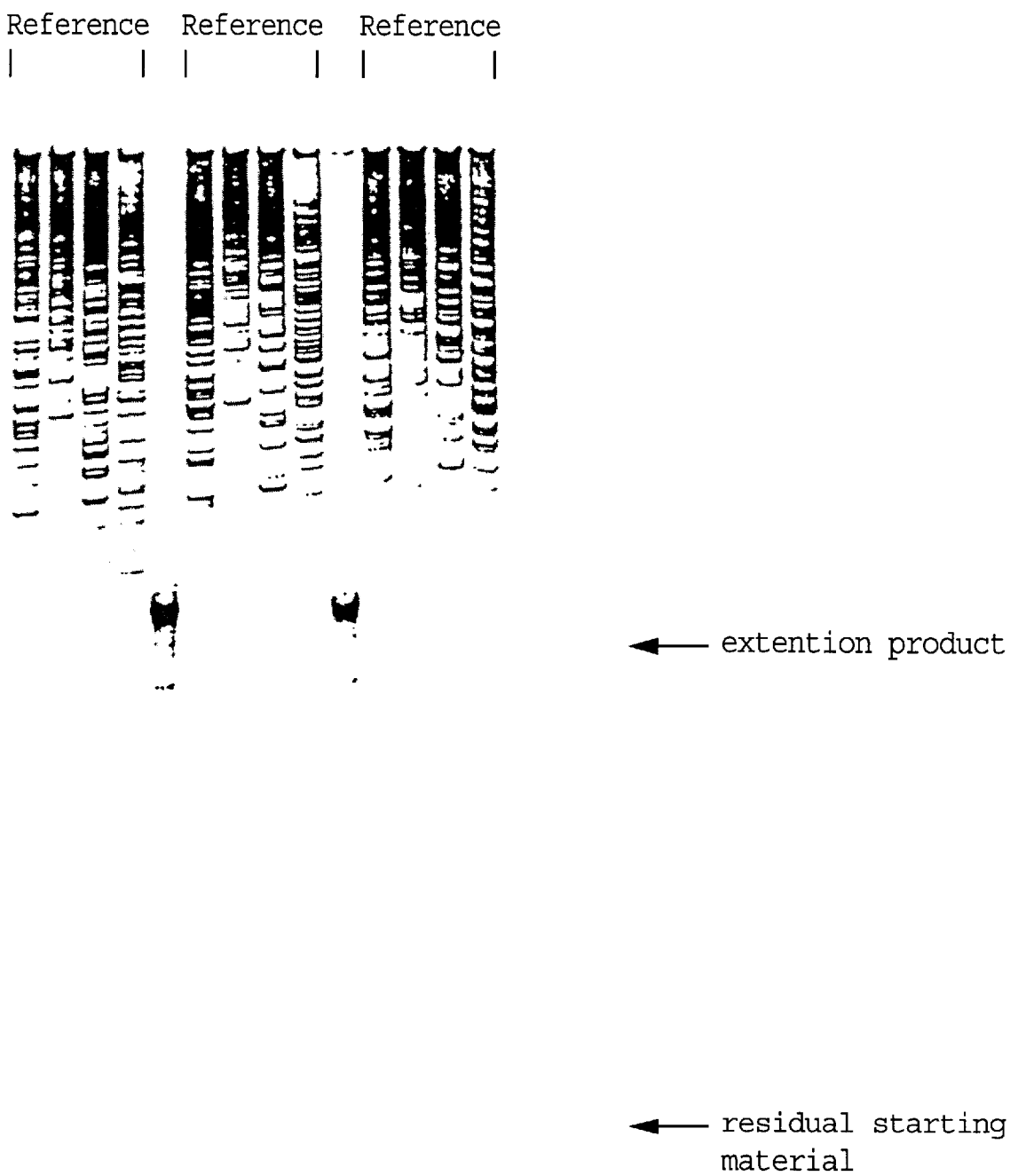
FIG. 8 is an autoradiograph of an acrylamide gel showing DNA in which all sugar-sugar linkages are phosphorothioate linkages.

Generation of all phosphorothioate DNA. A phosphorothioate 35-mer was generated by extending HO-GTAAAACGACGGCCAGT (SEQ ID No 3) (all phosphorothioate links). This primer sequence (2 μl 1 pmole/μl) was annealed to 4 μl template oligonucleotide (40-mer, ~200 ng/μl) 5'biotin-CAGGCATGCAAGCTTGGCACTGGCCGTCGTTTTAC AACGT (SEQ ID No 4)) with 2.5 μl TM buffer (100 mM Tris-HCl pH 8, 50 mM $MgCl_2$) and 17 μl TE buffer (10 mM Tris-HCl, 1 mM EDTA pH 8) at 55° C. in 30 min. 2 μl of 0.25 mM deoxycytidine 5'-α-thiotriphosphate (Sp-isomer), 0.25 mM deoxyguanosine 5'-α-thiotriphosphate (Sp-isomer), 0.25 mM thymidine 5'-α-thiotriphosphate (Sp-isomer) and $^{35}$S-deoxyadenosine 5'-α-thiotriphosphate (0.1 μCi) in TE buffer were added to the annealed oligonucleotides. 0.25 units of Klenow fragment were added and the mixture kept at 37° C. for 20 min. 2 μl of tracking dye were added. Samples were heated to 80° C. for 20 minutes to denature and reduce volume. The samples were then separated on a 15% acrylamide gel containing 8 M urea for 1–2 h (FIG. 8: 1–4, 6–9, 11–14 reference M13 sequence, 5 and 10 $^{32}$P-end labelled phosphorothioate M13 forward sequencing primer extended with α-S-dNTPs, extension terminates at the end of the template).

Figure 9:
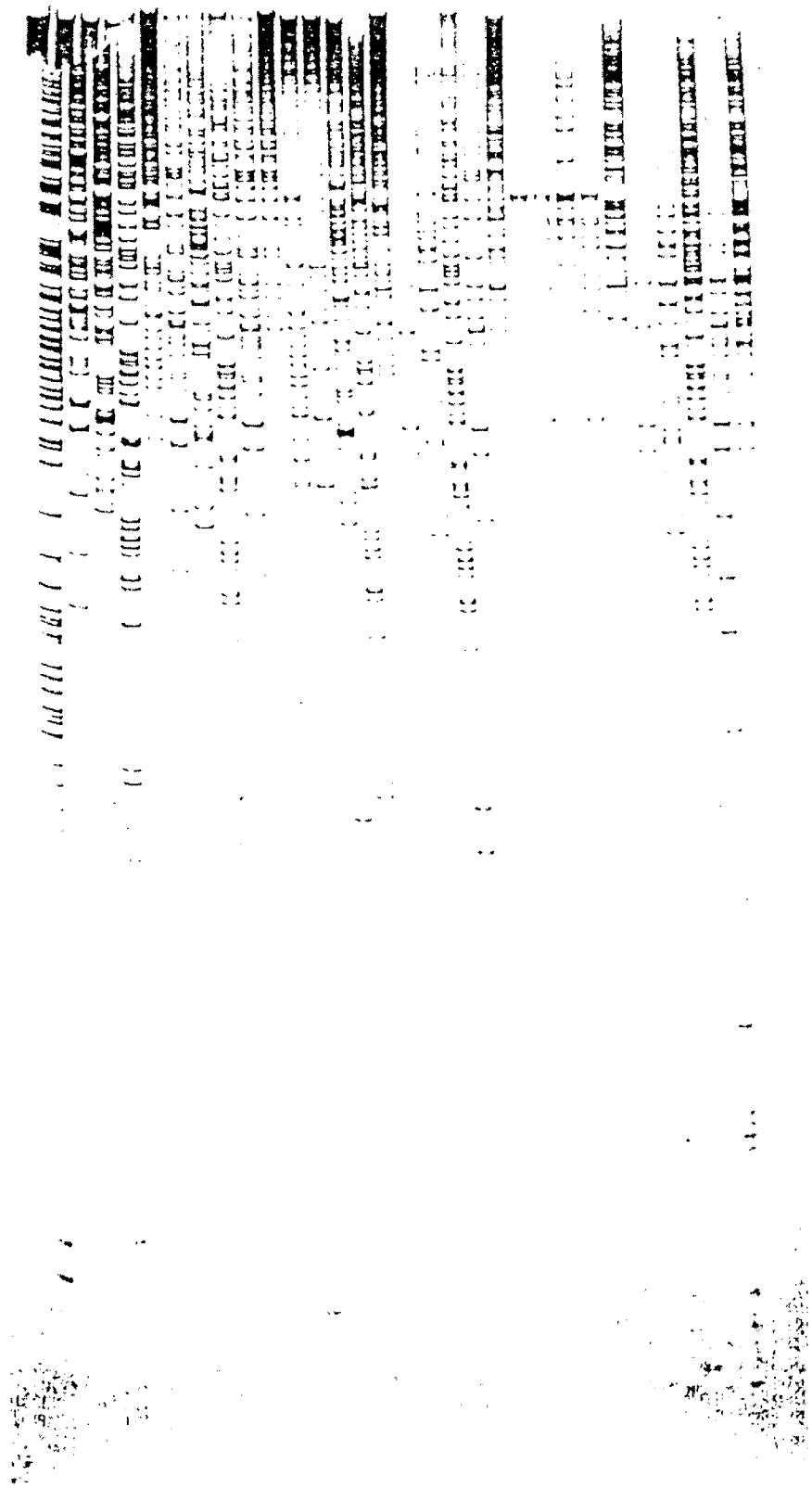
FIG. 9 is an autoradiograph of an acrylamide gel showing that ddCTPα-S can terminate a growing DNA chain.
Figure 10B:
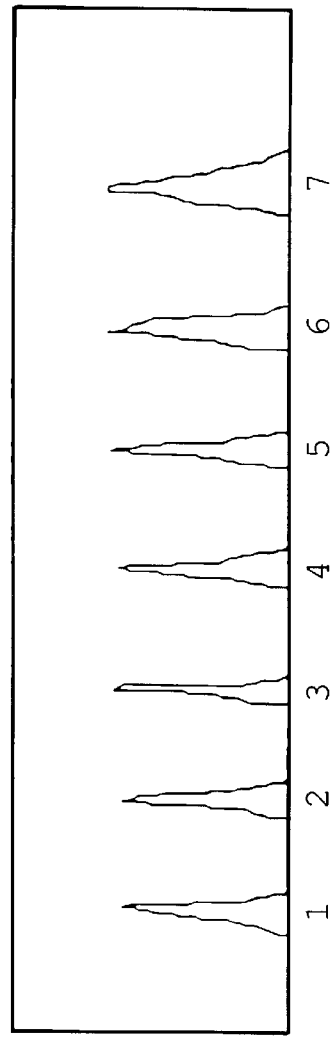
Figure 10D:
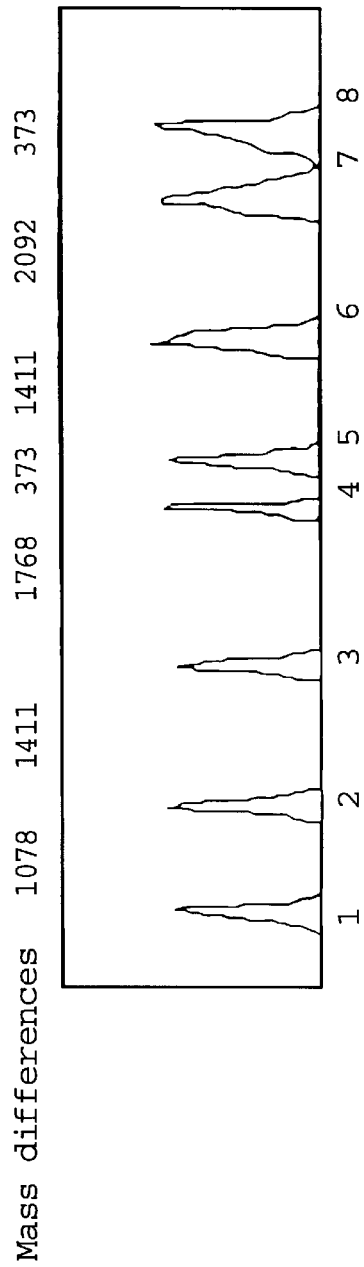
Figure 10F:
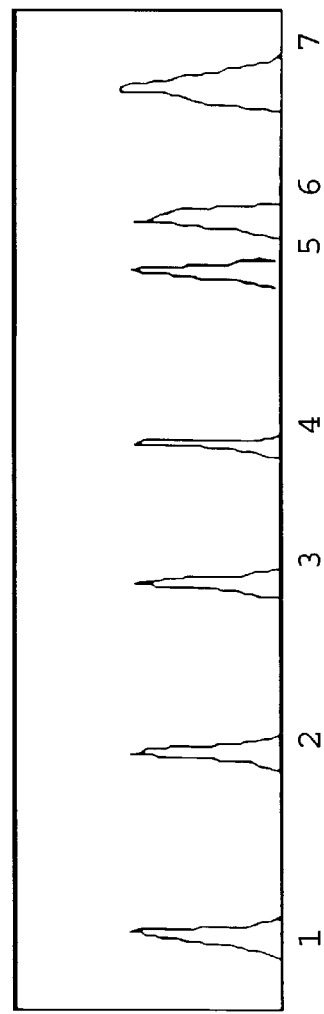
Figure 10H:
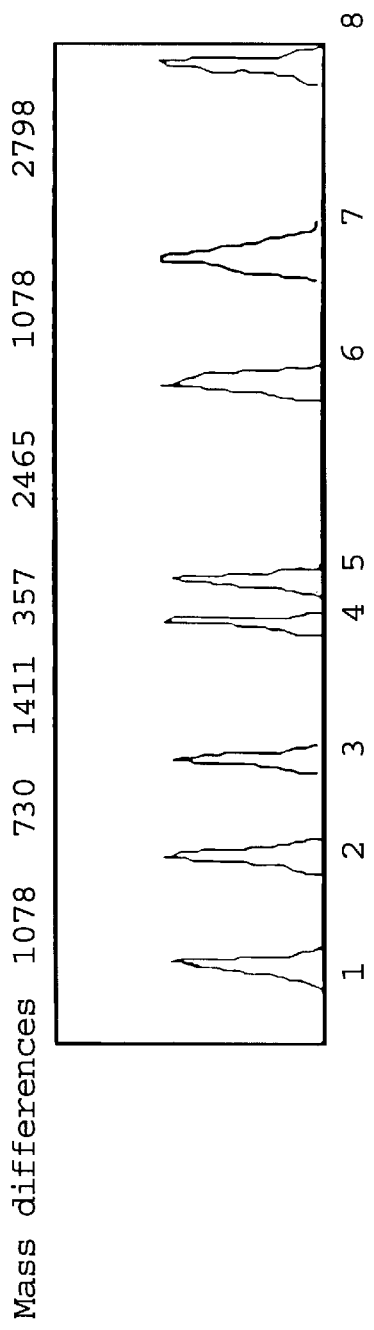

2 μl of M13 (purified by ethanol precipitation) was used per sample (200 ng/μl). 0.04 pmoles of M13 forward sequencing primer, 0.8 pmoles of M13 all phosphorothioate forward sequencing primer or 1 pmole of hexyl-M13 all phosphorothioate forward sequencing primer was added in 2 μl binding buffer containing 0.25 mM α-S-dTTP, 0.25 mM α-S-dGTP and 0.05 mM α-S-dCTP. Primers were annealed at 55° C. for 30 min. 0.2 μl of 2.5 mM ddTTP, 0.4 mM ddCTP, 0.8 mM ddGTP, 0.05 mM ddATP or 1.5 μl of 1.0 mM ddCTPα-S was added to appropriate samples. 2 ml of enzyme the same as for regular sequencing protocol was added. This procedure leads to complete phosphorothioate linked oligonucleotide fragments terminated with a ddCTP. α-S-dideoxycytidine triphosphate was incorporated roughly 10 times less efficiently as ddCTP but termination is just as specific (FIG. 9: tracks 1–10 regular M13 forward sequencing primer: 1–4 extension with regular nucleotide triphosphates (terminated TCGA), 5–8 extension with α-S-nucleotide triphosphates (termination TCGA), 9 extension with α-S-nucleotide triphosphates (termination C), 10 extension with α-S-nucleotide triphosphates (termination with α-S-ddCTP); tracks 11–20 phosphorothioate M13 forward sequencing primer: 11–14 extension with regular nucleotide triphosphates (terminated TCGA), 15–18 extension with α-S-nucleotide triphosphates (termination TCGA), 19 extension with α-S-nucleotide triphosphates (termination C), 20 extension with α-S-nucleotide triphosphates (termination with α-S-ddCTP); tracks 21–30 phosphorothioate hexyl M13 forward sequencing primer: 21–24 extension with regular nucleotide triphosphates (terminated TCGA), 25–28 extension with α-S-nucleotide triphosphates (termination TCGA), 29 extension with α-S-nucleotide triphosphates (termination C), 30 extension with α-S-nucleotide triphosphates (termination with α-S-ddCTP).

EXAMPLE 3

Chain Termination Protocol for Sequencing by MALDI Mass Spectrometry (Example with Phosphorothioate DNA, Alkylation Thereof and Removal of Primers a) PT primer (17–20 mer) or regular phosphate primer with a functionality for cleavage is annealed to a template DNA fragment. A biotinylated primer with a cleavage function may be used (to extract them from the mixture after polymerisation extension to improve resolution).

b) Extension with the four α-S-dNTPs, one of the four α-S-ddNTPs or one of the four ddNTP and a polymerase. Four parallel reactions (TCGA termination) give a mass ladder.

c) Optional step with biotinylated primer with cleavage facility. The extended product is extracted with a streptavidin coated medium (magnetic beads or surface) and removal of polymerases, α-S-dNTPs, α-S-ddNTPs and salts from the reaction. The products are washed and the cleavage function is triggered (eg backbone ethanol adduct can be cleaved at 95° C. under acidic conditions in 5 min) Gish & Eckstein (1990). Pure PT extension products are obtained. Alkylation may also be done before the extension products are cleaved from the primer. This allows purification after the alkylation reaction.

d) Addition of alkylation buffer and alkylating agent. Heating if necessary.

e) Mix with matrix material, spotting and drying (advantage of a volatile alkylating agent is that it is removed again at this stage).

f) Mass analysis of four parallel reactions terminated by each one of the four terminating functions. If regular ddNTPs were used analysis has to be done in negative ion mode, otherwise if the backbone is completely neutral analysis has to be done in positive ion mode.

FIG. 10 shows a diagrammatic representation of a DNA sequencing reaction using the methods of the invention.

EXAMPLE 4

Polymerase Chain Reaction Protocol for Analysis by MALDI Mass Spectrometry (Example with Phosphorothioate DNA, Alkylation Thereof, Removal of Primers)

a) 2 PT primers (17–20 mer) or regular phosphate with cleavage function (biotinylated primer with a cleavage function (Gish & Eckstein (1990) ethanol group attached to backbone, heating to 95° C. for 5 min under acidic condition leads to breakage of backbone) for purification after polymerisation). Primers are annealed to a template DNA fragment (50–60° C.).

b) Extension with 4 αS-dNTPs and a thermostable polymerase (37° C.).

c) Melting of polymerisation product and template (95° C.).

d) Annealing of primers to polymerisation product and template.

e) Cycling of process b)–d) (20 times) leads to the exponential amplification of the DNA.

f) Optional step with biotinylated primer with cutting facility. Extraction of extended product with a streptavidin coated medium (magnetic beads or surface) and removal of polymerases, αS-dNTPs and salts from the reaction.

Wash. Triggering of the cleavage function (only PT extension products are in supernatant). (Alkylation can also be done before the primers are cleaved off. This way the alkylation products can be cleared from reagents.)

g) Addition of alkylation buffer and alkylating agent. Heating if necessary. Here alkylating agents that do not alkylate the 3'OH are preferable.

h) Mix with matrix material, spotting and drying (advantage of a volatile alkylating agent is that it is removed again at this stage).

i) Mass analysis in positive ion mode. Two peaks are obtained one for each direction of PCR. Difference in mass of the two strands can be used for analysis (fingerprinting).

Figure 11B:
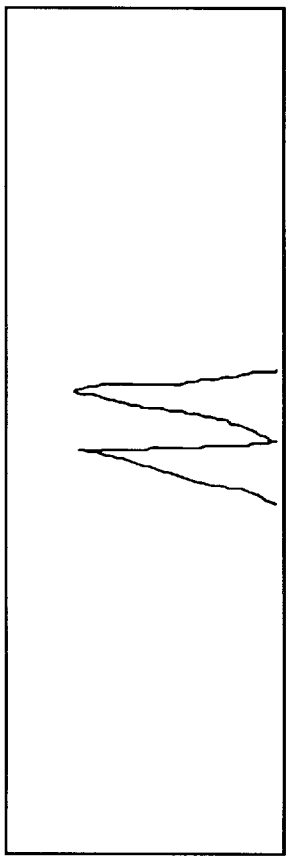

FIG. 11 shows a diagrammatic representation of a polymerase chain reaction using the methods of the invention.

EXAMPLE 5

Charge Tagging of DNA for Improved Analysis by Matrix-assisted Laser Desorption Time-of-flight Mass Spectroscopy In this Example we have developed methods for attaching quaternary ammonium tags to native and modified DNA. The efficiency of the chemistry was determined and protocols have been established by which the quaternary ammonium charge tags can be attached to synthetic oligonucleotides and PCR products either by a 5'$NH_2$ link or by attaching a base containing an aliphatic $NH_2$ group to the 3'end of DNA with terminal transferase or directly by using a base for termination in a Sanger protocol which has an aliphatic $NH_2$ group by which the charge tag can be attached to the sequence ladder. Alternatively the charge tag can be attached to the terminating base in a Sanger protocol prior to the chain extension. The efficiency of the detection of a charge tagged DNA was compared to similar oligonucleotides without the charge tag. It is estimated that the combination of charge tagging of an oligonucleotide combined with the alkylation of the backbone results in an increased detectability of oligonucleotides by a factor of 20. It was found that within an equimolar mixtures of differently modified oligonucleotides the charge tagged ones were predominant even when the mass spectrometric conditions are adjusted to optimised conditions for unmodified DNA. In addition the charge tagged and backbone neutralised oligonucleotides tend to suppress other oligonucleotides. Reaction side products in the matrix do not hamper the detectability of the charge tagged and backbone neutralised oligonucleotides.

In the work described in the previous Examples we showed the possibility of chemically post-modifying DNA to displace the negative charges of the sugar phosphate backbone prior to mass spectrometric analysis. Quantitative alkylation of an oligonucleotide reduces the number of gasphase events required. A single charge tag can be introduced into a synthetic oligonucleotide or into DNA generated enzymatically either via a terminating group or by enzymatically transferring a chemically reactive group (for example a base containing an aliphatic $NH_2$ group with terminal transferase).

Materials and Methods

Materials

Phosphorothioate oligonucleotides were synthesized using standard chemistry by an in-house DNA synthesis service: HO-GTCGACTCTAGAGGATC (SEQ ID No 39) M13 forward PCR primer, HO-GTCGACTCTAGAGGATC (SEQ ID No 39) M13 forward PCR primer(all phosphorothioatelinks), HO-GAATTCGAGCTCGGTAC (SEQ ID No 40) M13 reverse PCR primer, HO-GAATTCGAGCTCGGTAC (SEQ ID No 40) M13 reverse PCR primer (all phosphorothioate links), $NH_2$-TTTTTTTTTTTT (SEQ ID No 41) (all phosphorothioate links), $NH_2$-TCGATCGATCGA (SEQ ID No 2) (all phosphorothioate links), $H_2N$-TTT (all phosphorothioate links). HO-AGCT (all phosphorothioate links), hexyl-AGCT (all phosphorothioate links), $NH_2$-AGCT, $NH_2$-AGCT (all phosphorothioate links), AGCT-$NH_2$, AGCT-$NH_2$ (all phosphorothioate, HO-GTAAAACGACGGCCAGT (SEQ ID No 3) M13 forward sequencing primer, HO-GTAAAACGACGGCCAGTGCCAAGCTTGCAT (SEQ ID No 42) random 30-mer size standard. HO-CAGGCATGCAAGCTTGGCACTGGCCGTCGTTTT ACAACGT (SEQ ID No 43) random 40-mer size standard.

5'Hexyl phosphorotioate oligonucleotides were custom synthesized by Oswel DNA Service, University of Edinburgh (Edinburgh EH9 3JJ, UK) using standard phosphoramidite chemistry in conjunction with a hexyl building block which was linked via a phosphorothioate link: Hexyl-AGCT (all phosphorothioate links), hexyl-GTAAAACGACGGCCAGT (SEQ ID No 3) (all phosphorothioate links) M13 forward sequencing primer.

Deoxyadenosine 5'-α-thiotriphosphate (Sp-isomer), deoxycytidine 5'-α-thiotriphosphate (Sp-isomer), deoxyguanosine 5'-α-thiotriphosphate (Sp-isomer), thymidine 5'-α-thiotriphosphate (Sp-isomer) were purchased from Amersham (Little Chalford, UK). $C_2H_5I$ and matrices 2,2',4,4'-tetrahydroxybenzophenone, 6-aza-2-thiothymine, 2,4,6-trihydroxyacetophenone and 2,3,4-trihydroxyacetophenone were purchased from Aldrich (Gillingham, UK).

Trimethylammonium hexyryl-N-hydroxysuccinimidyl ester (C5-NHS) was synthesized according to the method of Bartlet-Jones et al, and was a gift of D. C. J. Pappin (Bartlet-Jones, M., Jeffrey, W. A., Hansen, H. F. and Pappin, D. J. C. (1994) *Rap. Commun. Mass Spectrom.* 8, 737–742).

5'End-labelling ($^{32}$P-dATP) of fully phosphorothioate linked oligonucleotides was done with T4 polynucleotide kinase (New England Biolabs) according to the protocol of Mundi et al (Mundi. C. R., Cunningham, M. W., Read. C. A. "Essential Molecular Biology: A practical approach", volume II, ed T. A. Brown, IRL Press, Oxford, 1991, 83–90). After endlabelling samples were precipitated to remove excess label.

For sequencing and termination Klenow fragment (Boehringer Mannheim) and for 3'terminal transfer of 3'$NH_2$-dideoxy thymidine triphosphate (Amersham) terminal transferase was used.

Oligonucleotides were separated on 20 cm×0.5 mm 15% acrylamide gels containing 8 M urea. They were run for 1–2 hours at 500 V after an initial run in at 200 V. Larger oligonucleotides were separated on 50 cm×0.5 mm 6%–10% acrylamide gels containing 8 M urea and are run for 4 h at 2000 V.

Mass spectrometry analysis (matrix assisted laser desorption ionization mass spectrometry (MALDI): 1 μl of a 1% solutions of matrix in 50% aqueous acetonitrile was spotted onto the target slide and air dried. 0.5 μl of samples was spotted on to the dried crystals. Dilutions of samples were done with 50% acetonitrile. Volatile components like solvents evaporate upon formation of the matrix. No further effort was made to remove residual buffer salts and salts that were side products of the alkylation reaction. This might lead to some suppression but in most cases no adverse effects were observed. Mass spectra were recorded on a Finnegan MAT LaserMat 2000 time-of-flight mass spectrometer, essentially as described by Mock et al (Mock, K. K., Sutton, C. W. and Cottrell, J. S. *Rapid Commun. Mass Spectrom.* (1992) 6, 233).

Methods

Attachment of a Quaternary Ammonium Charge Tag to an Oligonucleotide

Quaternary ammonium charge tags were attached to oligonucleotides via primary aliphatic amino groups according to FIG. 14. The reaction was equally as efficient when the amino group was on the 5' and 3' end of the oligonucleotide. Amino groups of the DNA bases were completely inert under the chosen reaction conditions. A solution of 1 µl of the amino substrate (10 mM), 9 µl of water and 0.5 µl of 2 M trimethylammonium/$CO_2$ buffer at pH=8.5 was prepared and put on ice. 8 µl of a 1% solution of $C_5$ trimethylammonium hexyryl-N-hydroxysuccinimidyl (C5-NHS) were added and left at 0° C. for 30 minutes. Thereafter excess reagent and the buffer were removed in vacuo at room temperature.

Combination of Charge Tagging with Alkylating the Phosphorothioate Backbone

The two step synthesis of alkylated phosphorothioate charge tagged DNA was performed as follows. Charge tagging was done first as the alkylating procedure would also take place with an aliphatic amino group. Charge tagging was done as described above. The reaction mixture was removed from ice after 30 minutes. 20 µl of 90% DMF was added then 1 µl of EtI and the tube placed in a waterbath at 55° C. for 30 minutes. Another 1 µl of EtI was added and the reaction mixture kept at 55° C. for a further 30 minutes. The solvent and volatile reagents were then evaporated and the product redissolved in 5 µl of 90% DMF. For MALDI MS analysis 1 µl of a 1% solution of the matrix is spotted onto the target slide and left to dry. 0.5 µl of the sample is then spotted on top of the dry matrix crystals. Dilutions of the products were done using 50% acetonitrile.

Terminal Transfer of a 3'$NH_2$-ddTTP Onto an Oligonucleotide

1 µl of a $^{32}$P kinased 17-mer oligonucleotide (regular and all phosphorothioate) was added to a solution of 1 µl terminal transferase (35 units), 8 µl of terminal transferase buffer (was supplied) and 23.5 µl $H_2O$. 1 µl of substrate was added (10 mM 3'$NH_2$-ddTTP or 10 mM dATP as control). The reaction was kept at 37° C. for 2 h. 3 µl of each sample was loaded onto a 15% acrylamide denaturing gel (FIG. 15)

Charge Tagging of a PCR Product

The chemically reactive group required for the attachment of charge tags to PCR products can be done in the same manner as described above for synthetic oligonucleotides (FIG. 16).

Charge Tagging of DNA Polymerase Ladder Fragments Using a 3'$NH_2$-ddNTP Terminator and a Ready Tagged Terminator with Klenow Polymerase 2 µl of M13mp18 template (~100 ng/µl), control primer mixes (10 µl dNTP-mix (standard protocol)+1.6 µl TM buffer+1.6 µl primer (M13mp18 at 0.2 pmoles/µl). 3'$NH_2$-ddTTP and charge tagged 3'$NH_2$-ddTTP were tested as terminators (10 mM). For the T tracks 1 µl of 0.5 mM dTTP, 20 µl of 0.5 mM dCTP, 20 µl of dGTP and 4 µl of TE buffer were mixed and aliquoted into 8×10 µl. To each aliquot 1.6 µl of primer, 1.6 µl of TM buffer and 1, 0.5, 0.25 or 0.125 µl of terminator was added. Of these mixes 2 µl was added to every 2 µl of template The samples were annealed for 30 min at 55° C. 2 µl of enzyme mix made up of 20 µl of $H_2O$, 3 µl of 0.1 M DTT, 2 µl of Klenow and 2 µl of $^{35}$S-dATP was added. The samples were kept at 37° C. for 20 min 2 µl of chase was added and samples were again kept at 37° C. for 20 min. 2 µl of denaturing loading buffer was added and samples denatured at 80° C. for 20 min. 6% acrylamide gel (FIG. 17). A schematic for this procedure is shown in FIG. 18. In place of the 3'$NH_2$ terminator the charge tagged $NH_2$ terminator can be used directly (data also shown in FIG. 17). dNTPs and primers can be replaced by αS analogues.

Matrices

As a charge is already present in the analyte in the form of a charge tag the desorption process no longer has to provide ionisation. Therefore any material can be used as a matrix that sufficiently absorbs at the excitation wavelength and can provide sufficient desorption.

MALDI MS Analysis of DNA Mixtures

The efficiency of the charge tagging procedure and the combination thereof with previously developed DNA backbone alkylation procedure was investigated. Twelve different 4-mers oligonucleotides with the sequence AGCT were investigated ($NH_2$-AGCT, $NH_2$-AGCT (all PT), AGCT-$NH_2$, AGCT-$NH_2$ (all PT), hexyl-AGCT (all PT), HO-AGCT (all PT), charge tagged $NH_2$-AGCT, charge tagged and backbone alkylated $NH_2$-AGCT (all PT), charge tagged AGCT-$NH_2$, charge tagged and backbone alkylated AGCT-$NH_2$ (all PT), backbone hexyl-AGCT (all PT), and backbone alkylated HO-AGCT (all PT)). The twelve oligonucleotides were investigated individually and in mixtures with different concentration ratios. Individually all twelve 4-mers could be detected. Analysis showed that the charge tagging reaction is clean and efficient. The removal of negative charges from the backbone by an alkylation reaction thereafter is also very efficient and clean. The combination of these two reactions is very simple. No side products were observed. Attaching a single positive charge via a charge tag has the advantage that there is no need for a high acidity in the matrix which leads to degradation of DNA.

When mixtures were prepared it was found that the interplay between the different 4-mers resulted in different detectability of each 4-mer. It was found that the charge tagged and backbone alkylated 4-mers dominated in detectability throughout. At equimolar preparation (30 fmoles of each 4-mer in the preparation) the charge tagged and backbone alkylated 4-mers were detected uniquely (Table 1 and FIG. 19). The addition of 5 mM tartaric diammonium salt, which is used to improve the resolution of unmodified oligonucleotide did not result in the detection of the unmodified 4-mers or the charge tagged but backbone unmodified 4-mers. Decreasing the concentration of the charge tagged and backbone alkylated 4mers (8 and 10 in Table 1) to 20% the concentration (5 fmoles in the preparation) of the others resulted in marginal detectability of charge tagged backbone unmodified 4-mers (7 and 9 in Table 1) but still 8 and 10 were predominant. Decreasing the concentration of the charge tagged and backbone alkylated 4-mers to 4% of the concentration (1.2 fmoles in the preparation) of the others resulted in the detectability of the backbone alkylated 4-mers without the addition of the ammonium salt and detectability of several of the other 4-mers after the addition of ammonium salt (see Table 1). Overall the charge tagged and backbone alkylated 4-mers were detectable with the same intensity using only 4% the amount of material. Therefore the sensitivity with this modification is increased roughly 20-fold.

TABLE 1

Effect of concentration of in mixtures of unmodified and modified 4-mer oligonucleotides

| sample number (measured masses) | modification or AGCT | 30 fmoles each | | 30 fmoles 1–7, 9, 11 and 12 6 fmoles 8 and 10 | | 30 fmoles 1–7, 9, 11 and 12 1.2 fmoles 8 and 10 | |
|---|---|---|---|---|---|---|---|
| | | nothing added | 10 mM NH$_4$ salt added | nothing added | 10 mM NH$_4$ salt added | nothing added | 10 mM NH$_4$ salt added |
| 1 (1382 Da) | 3'NH$_2$ | n | n | n | m | n | m |
| 2 (1447 Da) | 3'NH$_2$, all PT | n | n | n | n | n | n |
| 3 (1353 Da) | 5'NH$_2$ | n | w | n | w | n | m |
| 4 (1418 Da) | 5'NH$_2$, all PT | n | n | n | n | n | w |
| 5 (1402 Da) | 5'hexyl, all PT | n | n | n | n | n | n |
| 6 (1222 Da) | all PT | n | n | n | n | n | n |
| 7 (1537 Da) | charge tagged via 3'NH$_2$ | n | m | n | m | n | s |
| 8 (1713 Da) | charge tagged via 3'NH$_2$ all PT groups alkylated | s | s | s | m | m | n |
| 9 (1508 Da) | charge tagged via 5'NH$_2$ | n | m | n | s | n | s |
| 11 (1518 Da) | 5'hexyl, all PT groups alkylated | n | n | m | n | m | n |
| 12 (1308 Da) | all PT groups alkylated | n | n | m | n | m | n |

Table Caption

Effect of the variation of the relative concentrations within a mixture of twelve differently modified and unmodified 4-mers with the sequence AGCT, n=not detected, w=weak signal, m=medium strong signal and s=strong signal. The charge tagged and backbone alkylated 4-mers are equally well detected in mixtures at 20× lower concentration.

Thus, in conclusion of this Example we have developed methods by which after molecular biological generation of a DNA fragment selective chemistry can be used to attach groups that enhance the performance of the DNA for the applied detection technique. In our case we are specifically interested in enhancing the extractability and efficiency of ions of DNA for analysis by mass spectrometry. The selective chemical reaction between an aliphatic amino group and C5-NHS is used to link this compound that provides a single positive charge to a DNA fragment. Different ways are shown how this can be accomplished. The simplest being the use of a primer with a 5' amino group. Also the transfer of 3'NH$_2$-ddTTP onto the 3'-end of any DNA fragment can be used for the same purpose. 3'NH$_2$-ddTTP can also be used as a terminating group in a regular Sanger dideoxy sequencing approach using Klenow for polymerisation. It terminates specifically and efficiently. The combination of charge tagging with backbone alkylation and its benefits are demonstrated.

REFERENCES

[1] Karas, M. and Hillenkamp, F. (1988) *Anal. Chem.*, 60. 2299–2301.

[2] Gut, I. G. and Beck, S. (1995) In Griffin, H. and Griffin, A. (eds.) *Molecular biology: Current innovations and figure trends*, Horizon Scientific Press, Wymondham, UK, pp. 147–157.

[3] Nordhoff, E., Ingendoh, A., Cramer, R., Overberg, A., Stahl, B., Karas, M., Hillenkamp, F. and Crain, P. F. (1992) *Rapid Commun. Mass Spectrom.*, 6, 771–776.

[4] Nordhoff, E., Cramer, R., Karas, M., Hillenkamp, F., Kirpekar, F., Kristiansen, K. and Roepstorff, P. (1993) *Nucleic Acids Res.*, 21, 3347–3357.

[5] Pieles, U., Zürcher, W., Schär, M., Moser, H. E. (1993) *Nucleic Acids Res.*, 21, 3191–3196.

[6] Tang, K., Allman, S. L., Chen, C. H., Chang, L. Y. and Schell, M. (1994) *Rapid Comm. Mass Spectrom.*, 8, 183–186.

[7] Keough, T., Baker, T. R., Dobson, R. L. M., Lacey, M. P., Riley, T. A., Hasselfield, J. A., Hesselberth, P. E. (1993) *Rapid Commun. Mass Spectrom.*, 7, 195–200.

[8] Baker, T. R., Keough, T., Dobson, R. L. M., Riley, T. A., Hasselfield, J. A. and Hesselberth, P. E. (1993) *Rapid Commun. Mass Spectrom.*, 7, 190–194.

[9] Gish, G. and Eckstein, F. (1988) *Science*, 240, 1520–1522.

[10] Eckstein, F. and Gish, G. (1989) *Trends in Biochem. Sci.*, 14, 97–100.

[11] Cosstick, R., McLaughlin, L. W. and Eckstein, F. (1984) *Nucleic Acids Res.*, 12, 1791–1810.

[12] Hodges, R. R., Conway, N. E. and McLaughlin, L. W. (1989) *Biochemistry*, 28, 261–267.

[13] Labeit, S., Lehrach, H. and Goody, R. S. (1986) *DNA*, 5, 173–177.

[14] Nakamaye, K. L., Gish, G., Eckstein, F. and Vosberg, H.-P. (1988) *Nucleic Acids Res.*, 16, 9947–9959.

[15] Mundi, C. R., Cunningham, M. W., Read, C. A. (1991) In Brown, T. A. (ed.) *Essential Molecular Biology: A practical approach*. IRL Press, Oxford, Vol. 11, pp. 83–90.

[16] Mock, K. K., Sutton, C. W. and Cottrell, J. S. (1992) *Rapid Commun. Mass Spectrom.*, 6, 233–238.

[17] Fitzgerald, M. C., Zhu, L. and Smith. L. M. (1993) *Rapid Comm. Mass Spectrom.*, 7, 895–897.

[18] Heise, T. W. and Yeung, E. S. (1994) *Anal. Chem.*, 66, 355–361.

[19] Hettich, R. and Buchanan, M. (1991) In Standing, K. G. and Ens, W. (eds.) *Methods and mechanisms for producing ions from large molecules*. Plenum Press, New York, pp. 247–255.

[20] Hedin, A., Westman, A., Hakansson, P. and Mann, M. (1991) In Standing, K. G. and Ens, W. (eds.) *Methods and mechanisms for producing ions from large molecules*. Plenum Press, New York, pp. 211–219.

[21] Alderton, R. P., Eccleston, L. M., Howe, R. P., Read, C. A., Reeve, M. A. and Beck, S. (1992) *Anal. Biochem.*, 201, 166–169.

[22] Beck, S., Kelly, A., Radley, E., Khurschid, F., Alderton, R. P. and Trowsdale, J. (1992) *J. Mol. Biol.,* 228.
[23] Eckstein, F. (1983) *Angew. Chem.* 95, 431; (1983) *Angew. Chem. Int. Ed. Eng.* 22, 423.
[24] Olsen, D. B. & Eckstein, F. (1990) *Proc. Natl. Acad. Sci. USA* 87, 1451.
[25] Uznanski, B., Wilk, A. & Stec. W. J. (1987) *Tetrahedron Lett.* 28, 3401.
[26] Nemer, M. J. & Ogilvie, K. K. (1980) *Tetrahedron Lett.* 21, 4149.
[27] Nielsen, J., Brill, W. K-D. & Caruthers, M. H. (1988) *Tetrahedron Lett.* 29, 2911.
[28] Marcus-Sekura, C. J., Woerner, A. M., Shinozuka, K., Zon, G. & Quannan, G. V. (1987) *Nucleic Acids Res.* 15, 5749.

What is claimed is:

1. A method of analyzing a nucleic acid by mass spectrometry comprising the steps of
   (1) providing a positively charged or negatively charged nucleic acid molecule containing one or up to ten negative charges and no or up to ten positive charges, or no negative charges and one or up to ten positive charges, wherein the nucleic acid molecule has a sugar-linkage-sugar backbone and said sugars have a base attached thereto at the 1 position; and there are fewer negative charges than there are sugar-sugar linkages;
   (2) introducing the said nucleic acid molecule into a mass spectrometer; and
   (3) determining the mass of the said nucleic acid molecule.

2. A method of analyzing a nucleic acid by mass spectrometry wherein the nucleic acid molecule has a sugar-linkage-sugar backbone and said sugars have a base attached thereto at the 1 position; said method comprising the steps of
   (1) preparing a nucleic acid molecule comprising a negatively charged non-phosphate sugar-sugar linkage;
   (2) eliminating charge from the sugar-sugar linkages of the said nucleic acid molecule by covalent modification of the negatively charged non-phosphate sugar-sugar linkage so that the resulting nucleic acid molecule is positively charged or negatively charged and said molecule contains one or up to ten negative charges, being fewer charges than there are sugar-sugar linkages;
   (3) introducing the said nucleic acid molecule in which the charge has been partly eliminated as said into a mass spectrometer; and
   (4) determining the mass of the said nucleic acid molecule.

3. A method according to claim 2 wherein the said nucleic acid molecule has one phosphate sugar-sugar linkage.

4. A method according to claim 1 wherein the nucleic acid has one charge.

5. A method according to claim 1 wherein the nucleic acid DNA or an analouge or derivative thereof wherein the sugar residue comprises a 2'-deoxyribose.

6. A method according to claim 1 wherein the said mass spectrometry is matrix-assisted laser desorption ionization time-of-flight mass spectroscopy (MALDI MS).

7. A method according to claim 1 wherein when the nucleic acid is uncharged or positively charged the mass is determined by detection in positive ion mode.

8. A method according to claim 1 wherein when the nucleic acid is negatively charged the mass is determined by detection in negative ion mode.

9. A method according to claim 1 wherein a plurality of nucleic acid molecules with differing molecular mass are introduced into the mass spectrometer and the mass of at least one of the said molecules is determined.

10. A method according to claim 1 wherein an enzymatic chain extension step is used in the preparation of the nucleic acid.

11. A method according to claim 9 wherein a polymerase chain reaction is used in the preparation of the plurality of nucleic acid molecules.

12. A method according to claim 9 wherein a nucleic acid chain terminating reagent is used in the preparation of the plurality of nucleic acids.

13. A method according to claim 12 further comprising the step of determining a nucleotide sequence or detecting a mutation by comparing the mass differences of the said plurality of nucleic acid molecules.

14. A method of preparing a nucleic acid molecule containing no or up to ten negative charges or a nucleic acid molecule containing no or up to ten positive charges wherein the nucleic acid molecule has a sugar-linkage-sugar backbone and said sugars have a base attached thereto at the 1 position; said method comprising the steps of
   (1) synthesizing a nucleic acid with a phosphorothioate linkage or a phosphoroselenoate linkage between sugar residues, and
   (2) reacting the said nucleic acid with an alkylating agent so as to eliminate the charge on the said phosphorothioate linkage or said phosphoroselenoate linkage wherein step (1) further comprises (a) synthesizing said nucleic acid with a taggable group, said taggable group being capable of accepting a positive charge either directly or indirectly and either before or after step (2), or (b) synthesizing said nucleic acid with a precursor that comprises a positively charged moiety.

15. A method of preparing a positively charged or negatively charged nucleic acid molecule containing one or up to ten negative charges and no or up to ten positive charges or no negative charges and one or up to ten positive charges, said nucleic acid molecule comprising a sugar-linkage-sugar backbone wherein said sugars have a base attached thereto at the 1 position; said method comprising the steps of
   (1) enzymatically synthesizing a nucleic acid with a phosphorothioate linkage or a phosphoroselenoate linkage between sugar residues, and
   (2) reacting the said nucleic acid with an alkylating agent so as to eliminate the charge on the said phosphorothioate linkage or said phosphoroselenoate linkage, wherein said nucleic acid molecule consists of at least 4 nucleoside moieties.

16. A method of analyzing a nucleic acid by mass spectrometry comprising the steps of
   (1) providing a positively or negatively charged nucleic acid molecule obtainable by the method of claim 15, containing one or up to ten negative charges and no or up to ten positive charges, or no negative charges and one or up to ten positive charges, wherein there are fewer negative charges than there are sugar-sugar linkages;
   (2) introducing the said nucleic acid molecule into a mass spectrometer; and
   (3) determining the mass of the said nucleic acid molecule.

17. A method according to claim 14 wherein the nucleic acid with a phosphorothioate linkage or a phosphoroselenoate linkage is synthesized chemically.

18. A method according to claim 14 wherein the nucleic acid is synthesized by copying a nucleic acid template using a primer, a polymerase and dNTP-α-S or dNTP-α-Se.

19. A method according to claim 18 wherein the primer is an oligonucleotide wherein each of the sugar-sugar linkages is either a phosphorothioate or a phosphoroselenoate linkage.

20. A method according to claim 18 wherein the primer is positively charged.

21. A method according to claim 20 wherein the primer comprises an amino residue at its 5' end.

22. A method according to claim 18 wherein the primer is negatively charged which negative charge is not eliminated upon reaction with the said alkylating agent.

23. A method according to claim 22 wherein the primer comprises a phosphate as a sugar-sugar linkage.

24. A method according to claim 14 wherein each of the sugar-sugar linkages is either a phosphorothioate or a phosphoroselenoate linkage.

25. A method of preparing a nucleic acid molecule containing no or up to ten negative charges or a nucleic acid molecule containing no or up to ten positive charges wherein the nucleic acid molecule has a sugar-linkage-sugar backbone and said sugars have a base attached thereto at the 1 position; said method comprising the steps of
  (1) synthesizing a nucleic acid with a phosphorothioate linkage or a phosphoroselenoate linkage between sugar residues, and
  (2) reacting the said nucleic acid with an alkylating agent so as to eliminate the charge on the said phosphorothioate linkage or said phosphoroselenoate linkage, wherein the nucleic acid chain is synthesized enzymatically and is terminated using a ddNTP, a ddNTP-α-S or a ddNTP-α-Se.

26. A method according to claim 14 wherein the alkylating agent reacts selectively, but substantially completely, with the phosphorothioate S atom or phosphoroselenoate Se atom.

27. A method according to claim 14 wherein the alkylating agent reacts substantially completely with the phosphorothioate S atom or phosphoroselenoate Se atom and substantially completely with other reactive groups in the said nucleic acid.

28. A method according to claim 14 wherein the alkylating agent is any of R-Hal wherein R is any of a primary, secondary or tertiary alkyl, alkenyl, —CO-alkyl, —CO-aryl, —CH(Hal/Cl/F) alkyl, —CH(Hal/Cl/F)-aryl, —C(Hal/Cl/F)(Hal/Cl/F)alkyl and —C(Hal/Cl/F)aryl and wherein Hal is independently Br or I and (Hal/Cl/F) is independently any of Hal or Cl or F; or an alkene or vinyl such as $H_2C$=CH-alkyl and $H_2C$=CH-aryl.

29. A method according to claim 28 wherein the alkylating agent is any of methyliodide, methylbromide, ethyliodide, ethylbromide, propyliodide, propylbromide, butyliodide, butylbromide, 1-iodopropane2-one, 1-iodopropane-3-one, 1-bromopropane-2-one, 1-bromopropane-3-one, 1-iodo-2-fluoropropane, 1-iodo-2-chloro-propane, 1-bromo-2-fluoropropane and 1-bromo-2-chloropropane.

30. A method according to claim 29 wherein the alkylating agent is any of methyl iodide, ethyl iodide or propyl iodide.

31. A method according to claim 30 wherein the alkylating agent is ethyl iodide.

32. A method of preparing a nucleic acid molecule containing one or up to ten negative charges wherein the nucleic acid molecule has a sugar-linkage-sugar backbone and said sugars have a base attached thereto at the 1 position; said method comprising the steps of synthesizing enzymatically the said nucleic acid using a dNTP uncharged at least at the α-phosphorus position, wherein the nucleic acid is synthesized additionally using a primer and a polymerase and wherein the said dNTP uncharged at least at the α-phosphorus position is enzymatically incorporated into the said nucleic acid molecule.

Figure 12B:
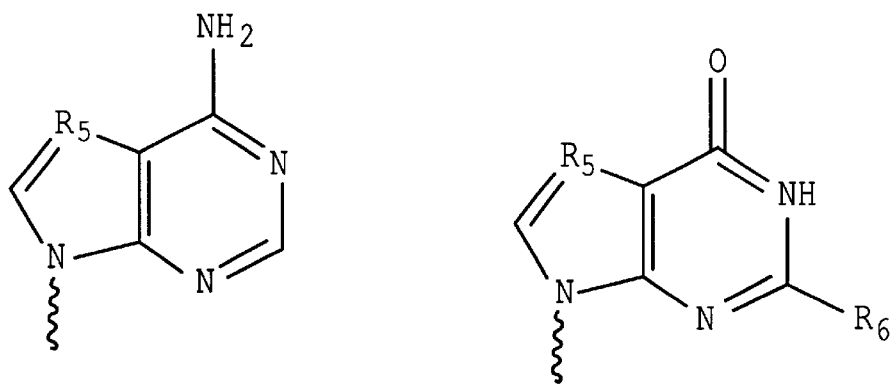

33. A method according to claim 32 wherein the uncharged dNTP is the dNTP shown in FIG. 12 wherein $R_3$ is H, $R_1$ is any of $BH_2$, $CH_3$, F, Cl or H, and $R_2$ is as given in FIG. 12.

34. A method according to claim 32 wherein the primer is an oligonucleotide wherein each of the sugar-sugar linkages is either uncharged or is phosphorothioate or a phosphoroselenoate linkage capable of having its charge eliminated.

35. A method according to claim 32 wherein the primer is positively charged.

36. A method according to claim 35 wherein the primer comprises an amino residue at its 5' end.

37. A method according to claim 34 wherein the primer comprises a phosphate as a sugar-sugar linkage.

38. A nucleic acid molecule comprising a sugar-linkage-sugar backbone wherein said sugars have a base attached thereto at the 1 position; said molecule further containing one to ten phosphate sugar-sugar linkages wherein all other sugar-sugar linkages are uncharged comprising at least 20 nucleoside residues.

39. A nucleic acid according to claim 38 comprising at least 50 nucleoside residues.

40. A nucleic acid with one or up to ten positive charges wherein the sugar-sugar linkages are uncharged.

41. A nucleic acid according to claim 40 wherein each sugar-sugar linkage is either an alkylated phosphorothioate moiety or an alkylated phosphoroselenoate moiety.

42. A method of analyzing a nucleic acid by mass spectrometry comprising the steps of
  (1) preparing a nucleic acid according to the method of claim 14;
  (2) introducing the said nucleic acid molecule into a mass spectrometer; and
  (3) determining the mass of the said nucleic acid.

43. A method according to claim 42 wherein the sugar-sugar linkages of the nucleic acid are substantially all phosphate sugar-sugar linkages.

44. A method according to claim 1, wherein said nucleic acid molecule comprises a non-phosphate sugar-sugar linkage.

* * * * *